US006745076B2

(12) United States Patent
Wohlgemuth et al.

(10) Patent No.: US 6,745,076 B2
(45) Date of Patent: Jun. 1, 2004

(54) IMPLANTABLE MEDICAL DEVICE WITH AUTOSENSITIVITY ALGORITHM FOR CONTROLLING SENSING OF CARDIAC SIGNALS

(75) Inventors: Peter Wohlgemuth, Neukirchen (DE); Henk A. Westendorp, Zutphen (NL); Harry W. M. De Bruyn, Arnhem (NL); J. Dave Munneke, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 334 days.

(21) Appl. No.: 09/987,777

(22) Filed: Nov. 16, 2001

(65) Prior Publication Data

US 2003/0097157 A1 May 22, 2003

(51) Int. Cl.[7] ............................................. A61N 1/362
(52) U.S. Cl. ......................................................... 607/27
(58) Field of Search .................. 607/9, 11, 27, 607/28, 29, 60; 128/901

(56) References Cited

U.S. PATENT DOCUMENTS

| | | | |
|---|---|---|---|
| 4,375,817 A | 3/1983 | Engle et al. |
| 4,379,459 A | 4/1983 | Stein |
| 4,384,585 A | 5/1983 | Zipes |
| 4,476,868 A | 10/1984 | Thompson et al. |
| 4,556,063 A | 12/1985 | Thompson et al. |
| 4,577,633 A | 3/1986 | Berkovits |
| 4,726,380 A | 2/1988 | Vollmann |
| 4,727,877 A | 3/1988 | Kallok |
| 4,800,883 A | 1/1989 | Winstrom |
| 4,830,006 A | 5/1989 | Haluska et al. |
| 4,880,004 A | 11/1989 | Baker et al. |
| 4,880,005 A | 11/1989 | Pless |
| 4,949,719 A | 8/1990 | Pless et al. |
| 4,953,551 A | 9/1990 | Mehra et al. |
| 5,010,887 A | 4/1991 | Thornader |
| 5,099,838 A | 3/1992 | Bardy |
| 5,103,819 A | 4/1992 | Baker et al. |

(List continued on next page.)

FOREIGN PATENT DOCUMENTS

| | | | |
|---|---|---|---|
| EP | 0 759 313 | 2/1997 | ........... A61N/1/365 |
| EP | 0 958 843 | 11/1999 | ............. A61N/1/37 |
| WO | WO92/18198 | 10/1992 | |

OTHER PUBLICATIONS

Olson et al. "Onset and Stability for Ventricular Tachyarrhythmia Detection in an Implantable Pacer–Cardioverter–Defibrillator" Computers in Cardiology, Oct. 7–10, 1986, IEEE Computer Society Press, p. 167–170.

*Primary Examiner*—George Manuel
(74) *Attorney, Agent, or Firm*—Girma Wolde-Michael

(57) ABSTRACT

A cardiac pacing system and method incorporate DSP processing and software algorithms for collecting signal amplitude data and noise data, and organizing the data for automatic checking of signal channel gain and signal detection sensitivity. Unfiltered signals are used to obtain values representative of maximum amplitude, which values are stored in a gain histogram, from which determination of the percentage of clipped signals can be made. Gain is adjusted by limiting clipping to a predetermined range of allowed clipping, to optimize use of the DSP range. The signals, both P waves and R waves for a dual chamber system, are also processed by DSP and parameters representing maximum amplitudes are stored in amplitude histograms. At the same time, noise is analyzed for respective windows of time following each ventricular event, and noise amplitude data is stored in noise histograms. After a predetermined waiting period, the signal amplitude and noise histograms are analyzed and compared, and for each channel the sensitivity is adjusted to fall between a calculated noise floor and the lowest bin of the amplitude histogram that contains valid data.

56 Claims, 16 Drawing Sheets

U.S. PATENT DOCUMENTS

| | | |
|---|---|---|
| 5,117,824 A | 6/1992 | Keimel et al. |
| 5,144,949 A | 9/1992 | Olson |
| 5,158,078 A | 10/1992 | Bennett et al. |
| 5,163,427 A | 11/1992 | Keimel et al. |
| 5,199,428 A | 4/1993 | Obel et al. |
| 5,207,218 A | 5/1993 | Carpentier |
| 5,312,453 A | 5/1994 | Shelton et al. |
| 5,314,430 A | 5/1994 | Bardy |
| 5,330,507 A | 7/1994 | Schwartz |
| 5,331,966 A | 7/1994 | Bennet et al. |
| 5,564,430 A | 10/1996 | Jacobson et al. |
| 5,620,466 A | 4/1997 | Haefner et al. |
| 5,685,315 A | 11/1997 | McClure et al. |
| 5,755,738 A | 5/1998 | Kim et al. |
| 5,800,465 A | 9/1998 | Thompson et al. |
| 5,891,171 A | 4/1999 | Wickham |
| 6,029,086 A | 2/2000 | Kim et al. |
| 6,029,087 A | 2/2000 | Wohlgemuth |

IMPLANTABLE MEDICAL DEVICE WITH AUTOSENSITIVITY ALGORITHM FOR CONTROLLING SENSING OF CARDIAC SIGNALS

FIELD OF THE INVENTION

This invention relates to medical device systems such as cardiac pacing systems and, more particularly, implantable systems the having the capability of sensing the occurrence of cardiac signals and distinguishing such signals from noise.

BACKGROUND OF THE INVENTION

Implantable medical devices such as cardiac pacemakers and defibrillators have a great need to accurately and reliably obtain cardiac signals, both for controlling the response and operation of the device and for collecting diagnostic information. This need results in placing substantial design importance on the ability to process such signals so as to determine when a genuine cardiac signal has been received, and to invalidate signals that represent noise or other artifacts. Thus, for an implantable pacemaker or pacemaker-cardioverter-defibrillator type device, it is important to sense all natural activity, including the wave components of normal conducted rhythms as well as premature ventricular beats (PVCs). But at the same time, it is important to distinguish artifacts, including muscle potentials; polarization; electromagnetic interference; lead artifacts; environmental electrical noise; and low level bio-electrical noise picked up by the system. This requirement of sensing the true signals and rejecting noise applies to each signal channel, e.g., both P waves and R waves for dual chamber pacemakers, as well as other signals in more complex systems.

The basic technique used in the pacemaker art is to establish a signal threshold, or sensitivity level, that is below the expected signal level for the signal being sensed, but above the normal noise level. Take as an example the task of detecting R waves of a normal amplitude range of 2.5 to 5.0 mV, with a signal channel having a noise level in the range of 0.25 to 1.0 mV. In such case, the threshold for a signal may be set somewhere between 1.5 and 2.0 mV, so as to eliminate detection of noise but insure sensing of valid signals. However, a problem is that signal levels will change, as will noise levels, in which case the sensitivity, or signal threshold, must be adapted accordingly. The prior art has shown many designs for doing this, most of which employ some manner of collecting signal and amplitude data and adjusting the threshold to stay above the noise level indicated by the recent data. Another problem that must be dealt with is that of adjusting gain so as to avoid excessive clipping of the signals, and to make the full amplifier range available for signal detection. If there is excessive clipping, then it is not possible to obtain an accurate profile of signal amplitudes. Further, if morphology analysis is to be used in event identification, then it is critical to contain clipping to within certain limits. Accordingly, the need in the art is to adjust gain in order to optimize amplification without too much distortion, and to adjust sensitivity in order to discriminate the true signals from noise.

A major problem that continues to confront design in this area is how to optimize the use of data so as to efficiently and reliably distinguish valid event signals from noise or other artifacts. Some prior art systems vary threshold on the basis of the signal and noise measurements of the last cycle, but such a technique is vulnerable to making adjustments in response to incidental artifacts and noise occurrences. Even systems that accumulate and average data over more than one cycle usually do not collect and process the data in a way that permits optimum profiling of signal amplitudes and noise.

Examples of prior art medical device systems with gain control or sensitivity adjustment schemes are found in the patents listed in Table 1 below. Note that it is not admitted that any of the patents listed in Table 1 necessarily constitute prior art with respect to the present invention.

TABLE 1

| Patent No. | Inventor(s) | Issue/Publication Date |
| --- | --- | --- |
| 4,880,004 | Baker et al | Nov. 14, 1989 |
| 5,010,887 | Thornander | Apr. 30, 1991 |
| 5,103,819 | Baker at al | Apr. 14, 1992 |
| 5,564,430 | Jacobson et al | Oct. 15, 1996 |
| 5,620,466 | Haefner et al | Apr. 15, 1997 |
| 5,685,315 | McClure et al | Nov. 11, 1997 |
| 5,755,738 | Kim et al | May 26, 1998 |
| 5,891,171 | Wickham | Apr. 6, 1999 |
| 6,029,086 | Kim et al | Feb. 22, 2000 |

All patents listed in Table 1 above are hereby incorporated by reference herein in their respective entireties. As those of ordinary skill in the art will appreciate readily upon reading the Summary of the Invention, Detailed Description of the Preferred Embodiments and Claims set forth below, many of the devices and methods disclosed in the patents of Table 1 may be modified advantageously by using the teachings of the present invention.

SUMMARY OF THE INVENTION

The present invention has a number of objects relative to the current state of the art. The various embodiments of the present invention provide solutions to one or more problems existing in the area of medical devices and, more particularly, implantable medical device systems and methods for accurately and reliably sensing and identifying patient cardiac signals.

One object of the invention is to provide one or more signal channels for sensing cardiac signals, and for obtaining and storing sample data representative of signal amplitude and noise amplitude over a period of time, the data being sampled and arranged so as to optimize calculation of channel sensitivity to discriminate valid signals from noise. The object is achieved by sampling both signal and noise amplitudes over time periods long enough to avoid distortion of information due to transient noise or artifacts, and storing the data over time periods suitable for accumulating sufficient data from which to accurately determine the current signal amplitudes and noise amplitudes so they can be compared.

Another object of the present invention is to arrange the sampled data in a form that enables efficient comparative analysis of the signal and noise data, and periodic adjustment of the data to reduce the long term historical impact of prior data, thereby continuously providing updated data that reflects true changes in the level of the patient signals without being unduly influenced by recent artifacts or past signal levels. The end objective of the signal and noise data analysis is periodic adjustment of the sensitivity level of the signal channel.

Another object of the present invention is to provide gain adjustments that accompany the sensitivity adjustments, the gain adjustments being based on collected signal data that contains information relating to signal clipping. The gain data and gain adjustments are preferably carried out in a manner that enables accurate adjustment of the sensitivity level to correspond to any change in gain level.

In accord with the above objects, there is provided a system and method of obtaining and processing signal data, adapted for use in one or more channels of a medical device such as a pacemaker or other implantable cardiac device. The system is based on using DSP circuitry that provides filtered and unfiltered wave signal and noise signal parameters, which parameters are stored and processed by a microprocessor system to determine desired adjustments in channel gain and sensitivity setting. The system employs the construction of three histograms for each signal channel. A first histogram is built to store data representative of unfiltered signal amplitudes, which data is used to determine percentage of signal clipping in order to indicate desired gain adjustment. Gain is suitably adjustable to one of a predetermined number of levels, and the gain histogram has a corresponding number of bins, each bin representing unfiltered maximum signal amplitudes within an amplitude range. The histogram bin widths are set so that the percentage of clipped signals can be easily determined, providing a basis for gain adjustment. The histogram bins match the gain settings. Each gain adjustment is accompanied by a shift of the data in the histogram bins so that the resulting bin data corresponds to the new gain.

In another embodiment, a quick gain adjustment feature is provided, in order to provide quicker response to changes in the cardiac signal levels during the acute situation just following implant of the device. This feature can be programmed for a predetermined period, for example, a week or two, and is based simply on adjusting gain whenever a predetermined percentage of clipping has been found over a given time period, or given number of signal events.

A second histogram is continuously maintained to provide signal amplitude data received from the DSP circuitry. The signal amplitude data is taken a programmable sample intervals, e.g., every 6 minutes, designed to be long enough to avoid the influence of bursts of invalid signals. The signal amplitude data is collected in the signal histogram over a period of time set to provide statistically valid data, e.g., every 7 days. Concurrently, noise data is sampled at the same intervals, and stored in a noise histogram. When the 7 day interval is timed out, and sufficient data has been collected, the signal and noise histograms are compared, and an algorithm determines whether an adjustment in channel sensitivity is indicated. If such an adjustment is indicated, it is made, and the corresponding new digital threshold levels are set in the DSP circuitry. The gain adjustment routine is coordinated with the sensitivity adjustment.

The object of optimizing use of signal and noise data is facilitated by the technique of building three histograms for each signal channel of the system. The influence of data over time can be determined by dividing the contents of each histogram by a predetermined factor (multiplying by a factor less than 1) following each new gain and sensitivity analysis. Alternately, past bin data can be adjusted by keeping only counts above a certain level. The histogram data is of a form that it can be efficiently analyzed to avoid basing the sensitivity settings on statistically insignificant samples.

DESCRIPTION OF THE PREFERRED EMBODIMENTS

Figure 1:
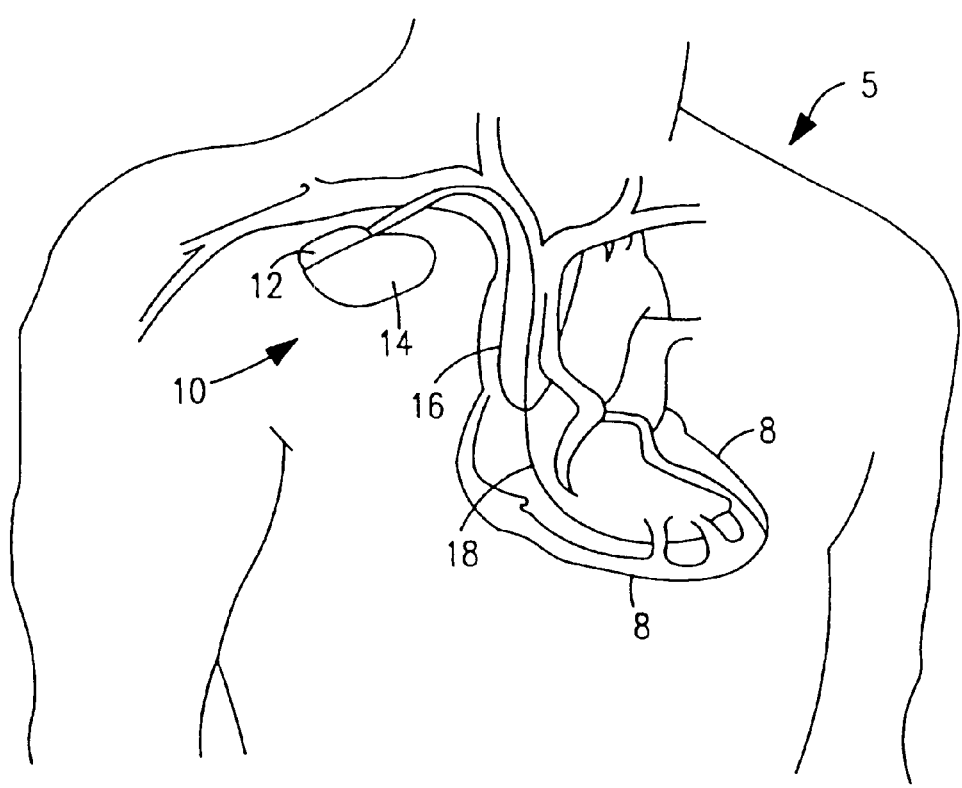
FIG. 1 is a simplified schematic view of one embodiment of implantable medical device ("IMD") of this invention.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
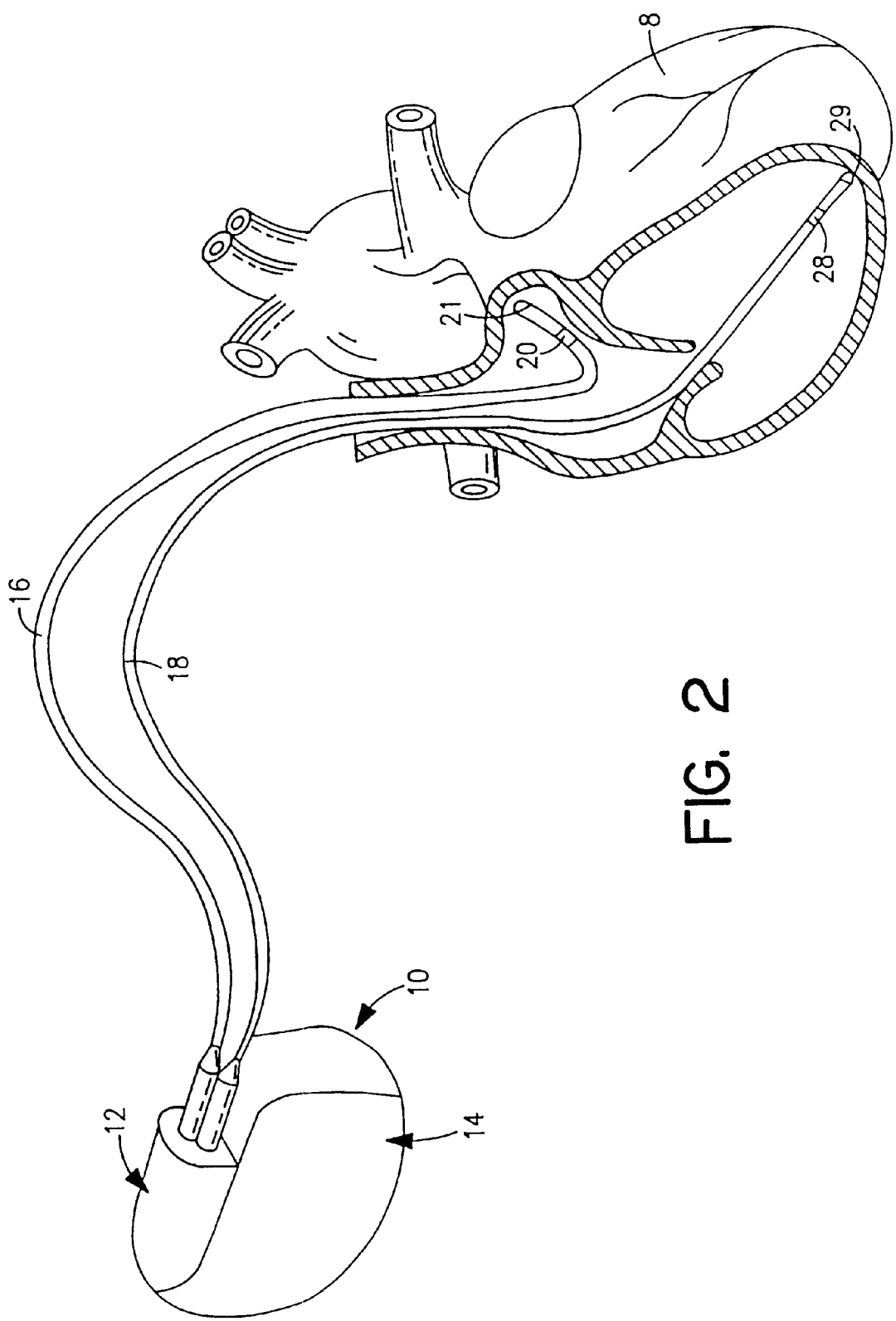
FIG. 2 is a schematic view showing a pacemaker form of IMD interconnected by a lead system with a heart.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
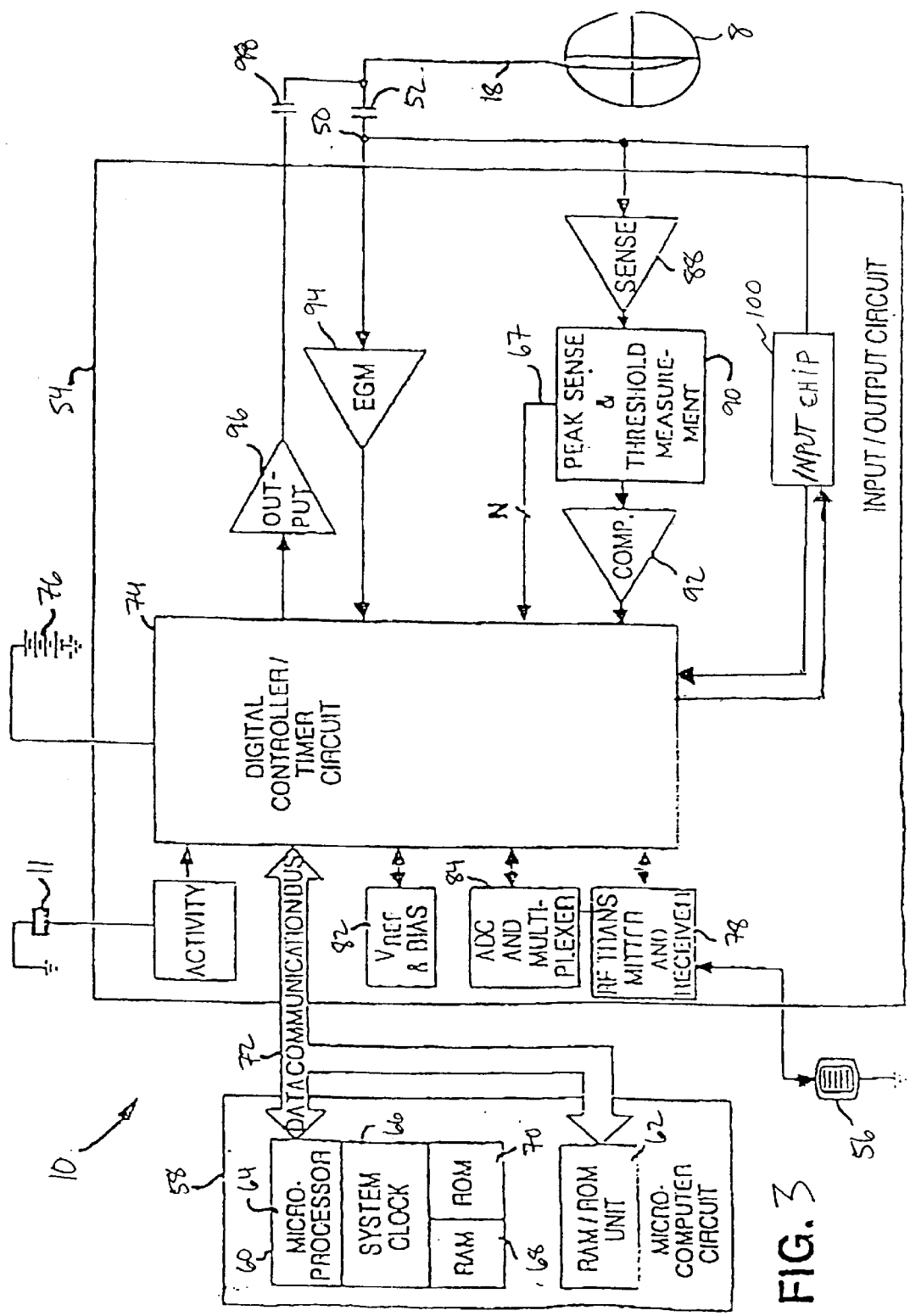
FIG. 3 shows a block diagram illustrating the primary constituent parts of an IMD that is a pacemaker having a microprocessor-based architecture.

FIG. 3 shows a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored in microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. In the preferred embodiment, signals from the patient's heart are coupled to an input channel chip shown at 100, which chip provides outputs to the controller 74. The preferred embodiment of this chip incorporates DSP circuitry, as discussed in connection with FIGS. 6A and 6B below, and as is further disclosed in U.S. Pat. No. 6,029,087, incorporated herein by reference. The specific embodiments of the input and output circuits illustrated in FIG. 3 may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all hereby incorporated by reference herein, each in its respective entirety.

Figure 4:
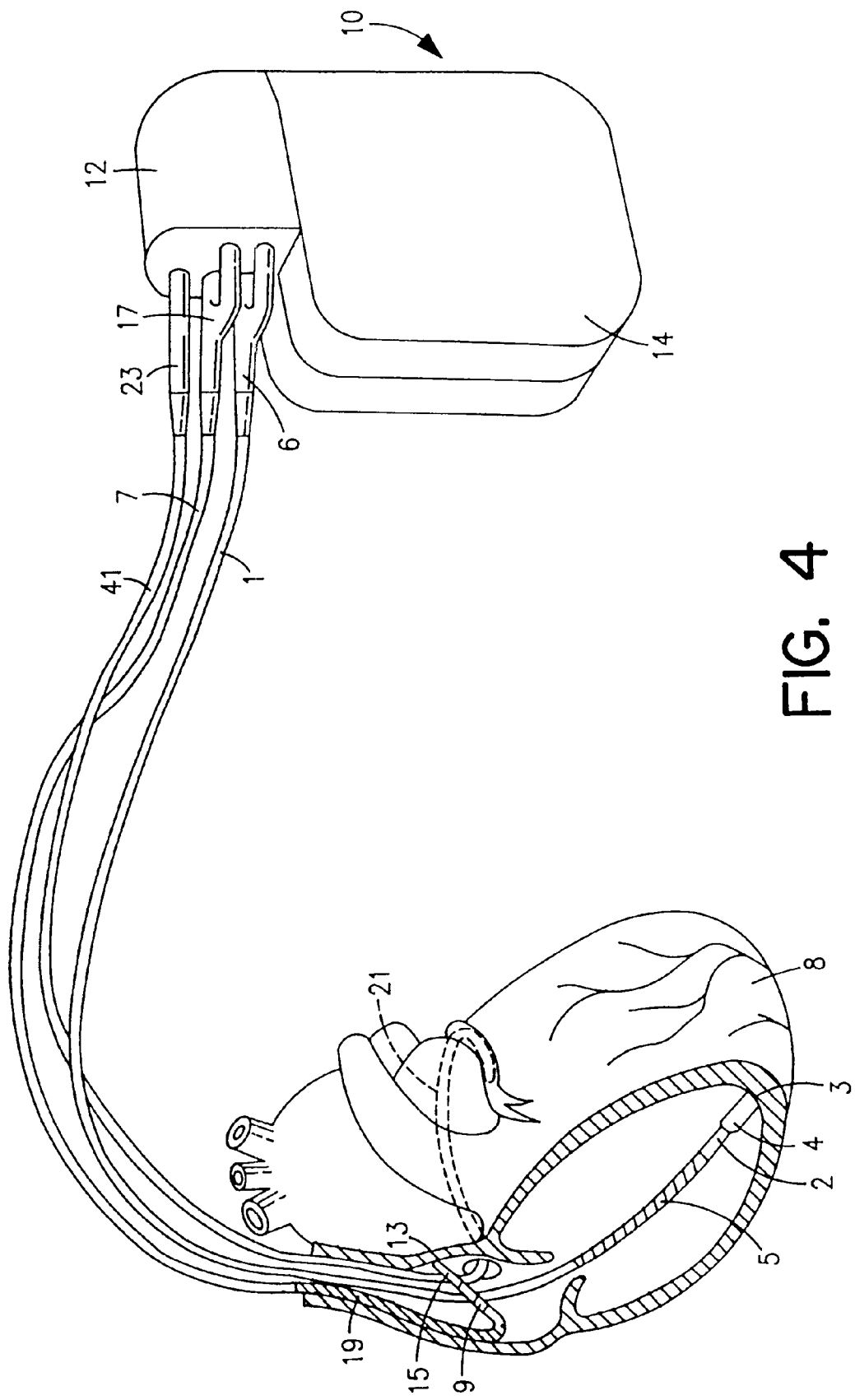
FIG. 4 is a schematic view showing a PCD form of IMD interconnected by a lead system with a heart.
Figure 5:
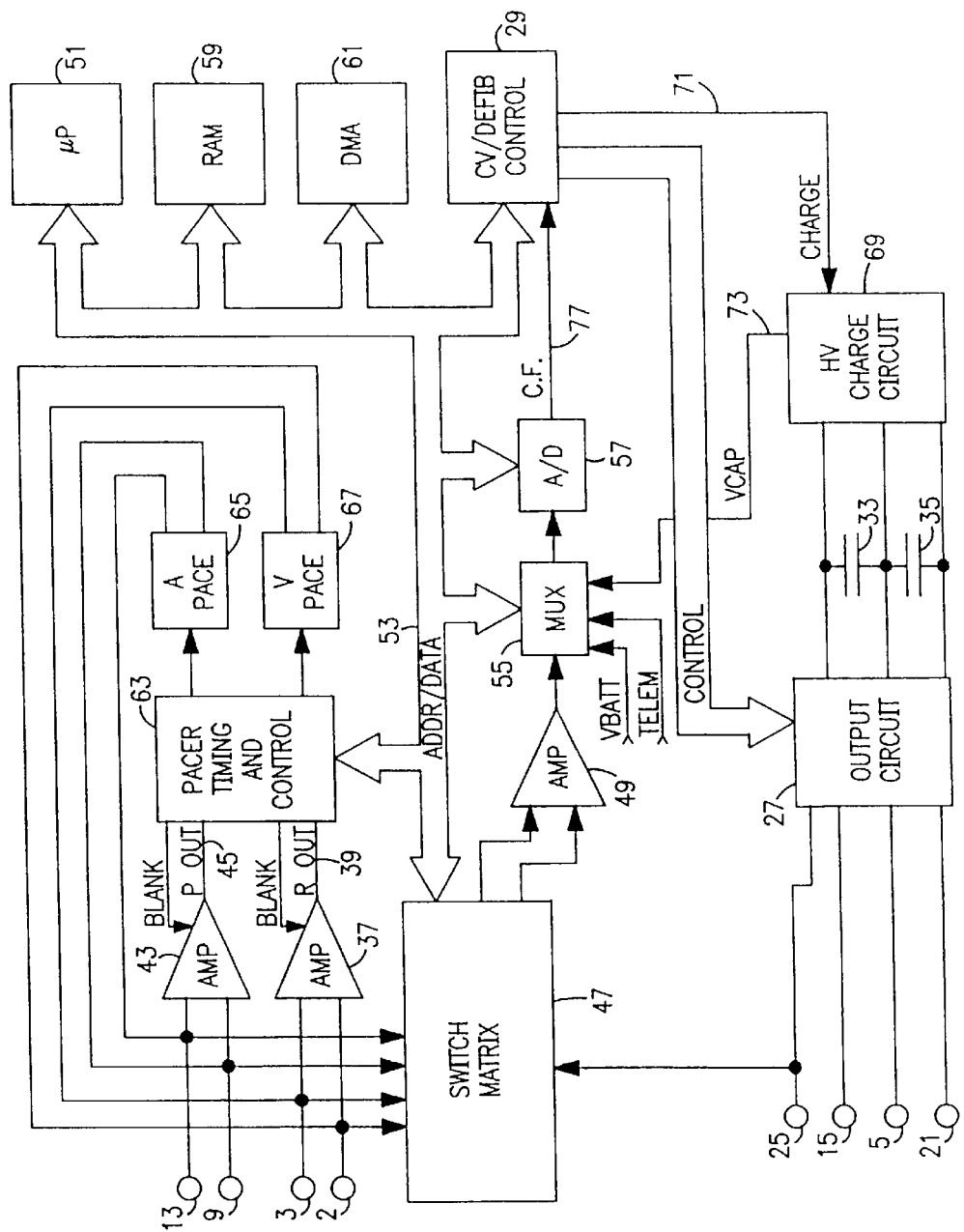
FIG. 5 is a functional schematic diagram of an IMD that is a PCD having a microprocessor-based architecture.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT U.S. application Ser. No. 92/02829, Publication No. WO92/18198, by Adams et al., and in the article "Automatic Tachycardia Recognition", by Arzbaecher et al., published in PACE, May–June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to a cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

The following description of preferred embodiments is equally applicable to auto sensing control for both P waves and R waves. The invention may likewise be utilized for sensing of T waves, although event sensing and the chosen parameters are different for T waves. The primary differences in comparing algorithms for automatic P wave sensitivity adjustment as compared to R wave sensitivity adjustment are:

(1) For P wave sensing, a separate amplitude histogram for fibrillation is preferably used, so that the data in the normal amplitude histogram is not distorted by fibrillation episodes;

(2) For P wave sensing, the timing of sensing and analysis must take into account the potential for far-field R wave (FFRP) sensing; and (3) Noise measurements are carried out at different times for the two respective signals.

The following description illustrates automatic control of sensitivity for the sensing of R wave events but unless noted otherwise is equally applicable to use of this invention for sensing of P waves. In certain instances, e.g. the discussion of the timing of sensing of both signals and noise, differences in the algorithms for auto adjustment of sensitivity will be discussed.

Figure 6A:
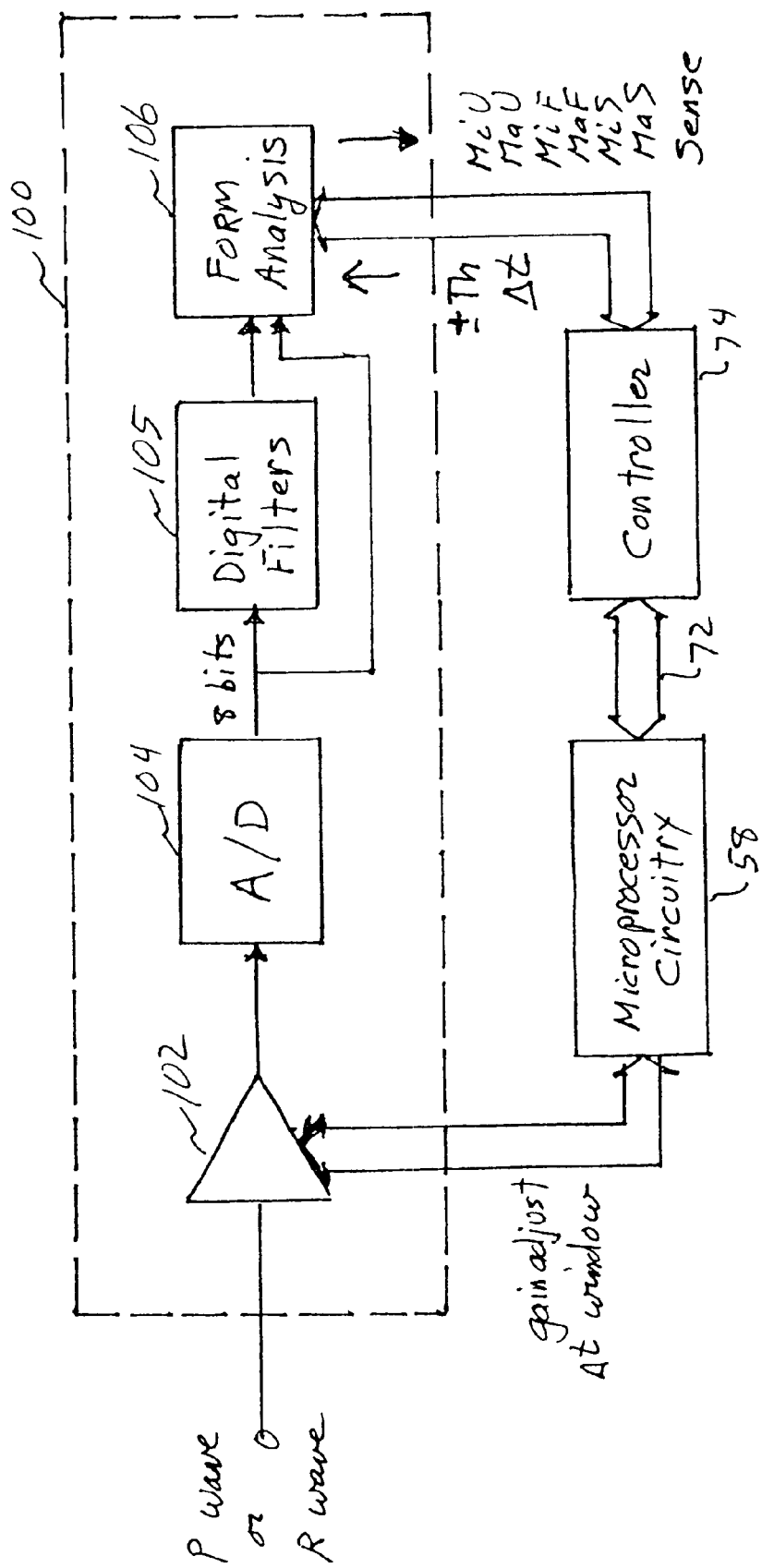
FIG. 6A is a block diagram showing the primary functional components of an input chip that includes DSP circuitry, for providing a signal channel in accord with this invention, the chip being interconnected with the microprocessor and controller of the IMD.
Figure 6B:
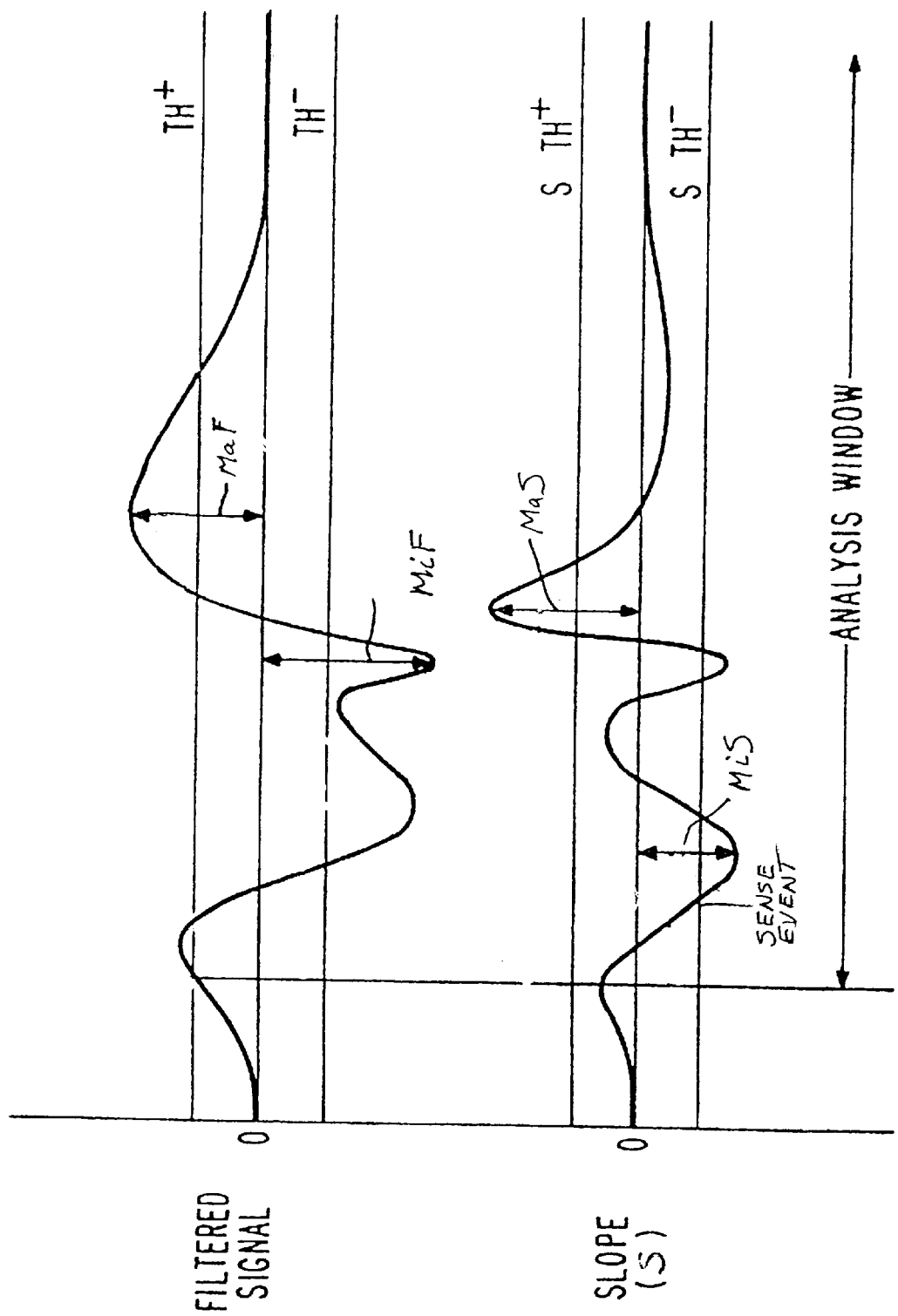
FIG. 6B shows curves of filtered and unfiltered signals, and the parameters provided by the DSP channel.

FIG. 6A shows a block diagram of some of the hardware components utilized in the operations of receiving and operating on input signals in accordance with the system and method of this invention for sensitivity control. The input signal, indicated as either a P or Rwave, is connected from the patient's heart to the input terminal of a chip 100 that preferably contains digital signal processing (DSP) circuitry. See referenced U.S. Pat. No. 6,029,087 for a full discussion of the component parts and characteristics of a DSP chip suitable for use in implantable medical devices. As indicated in referenced patent, the chip may have plural channels, e.g. separate processing channels for P, R and Twaves. In FIG. 6, a single channel is shown for ease of illustration. It is to be understood that other forms of this chip may be utilized, e.g., some of the operations may be carried out by analog circuitry. The signal is connected to adjustable gain amplifier 102, which has a gain that can be programmed to any of a set of fifteen (15) fixed values. These values, as discussed further below, are suitably set to exponentially increasing values, using as a base the square root of 2. The output of the amplifier is fed into an A to D converter circuit 104, which provides an 8-bit output for each sample of the signal being received. The A/D converter is followed by digital filters 105, that generate both a filtered signal and a slope signal, as illustrated in FIG. 6B. The filtered and unfiltered signals, together with the slope signal, are inputted to Form Analysis block 106, which produces the following output signals:

| | |
|---|---|
| MaU | Maximum of Unfiltered signal |
| MiU | Minimum of Unfiltered signal |
| MaS | Maximum of Slope signal |
| MaF | Maximum of Filtered signal |
| Mis | Minimum of Slope signal |
| MiF | Minimum of Filtered signal |

The six output signals are connected through to controller 74 and passed on across bus 72 to the microprocessor 58. Following analysis of the output signals provided from Form Analysis unit 106, the gain of amplifier 102 may be adjusted accordingly. The time window (Δt window) when amplifier 102 is enabled for amplification of received P or R signals is also adjustable under control of the microprocessor circuitry. When a new threshold level is determined, in accordance with the algorithms of this invention, the new value of digital threshold signal is passed from microprocessor circuitry 58 through controller 74 back to the DSP unit 100, so that the adjusted threshold levels, plus and minus, are available for use in the Form Analysis block 106. Similarly, time windows, indicated as Δt for use in different algorithms as discussed below are transmitted through to the DSP chip 100. The sense event signal, indicating a detection of a P wave or R wave, is also communicated from the Form Analysis block 106 through to the microprocessor. It is to be noted that block 106 illustrates a generic operations block for carrying out the operations of determining the designated outputs. However, for example, the event sensing operation may be carried out separately from the determination of the filtered and unfiltered output signals.

Event signal histograms collect all of natural activities, either normal conducted R waves (including ventricular extra systoles); and P waves. The aim is to optimize threshold based upon these natural activities and not on sensed artifacts such as interference. A DSP signal sense is defined by a combination of threshold crossings of filtered and slope signals in the channel where the operation takes place. A unipolar sense requires the filtered and the slope signal to drop below a certain negative threshold. A bipolar sense requires that both a filtered signal and a slope signal cross a threshold, either positive or negative.

FIG. 6B shows two signals obtained from the DSP digital filters 105. The curves of this Figure are illustrative of the DSP operation, and are not meant to represent any particular cardiac signal. The upper curve of FIG. 6B represents a filtered version of the signal from the A/D converter, and is what is referred to as the filtered signal. The bottom curve is the derivative, or the slope signal (S). The Th+ and Th− lines show the plus and minus thresholds that are established by digital settings. These are the symmetrical threshold values that are to be automatically adjusted in accord with this invention and which are utilized in determining whether or not an event has occurred. As indicated, an analysis window is initiated at the first threshold crossing, which is seen when the filtered signal crosses the Th+ line in the upper curve. The Form Analysis circuit operates for the duration of the window and generates the MiU, MaU, MiF, MaF, MiS and MaS signals. In the Figure, the filtered signal is assumed to have the same form as the unfiltered waveform. The MiF signal is the minimum value of the filtered signal, as shown; the MiU (not shown) signal is taken at the same point of the unfiltered signal. MaF is illustrated as the maximum value of the filtered waveform; MaU (not shown) is measured at the same point on the waveform. The upper curve also shows an example of obtaining the width (W) of a curve, here illustrated as being the time duration between the first and last crossing of the upper threshold. This is shown for illustration only, it being understood that other definitions of determining wave length or width can be adopted within the scope of this invention.

The lower curve illustrates MiS, the most negative point on the slope curve, and MaS, which is the highest, or most positive point on the slope curve. The same symmetrical threshold values are used, shown as "S Th+" and "S Th−". As discussed further below, a "sense event" is recognized when each of the curves has passed through a threshold. In the illustration of FIG. 6B, the filtered signal curve first passes through the + threshold, and the event is deemed to happen when the slope curve drops down to the S Th− level.

The method of this invention, which is illustrated by the algorithms described in detail below, utilizes the collection of data into histograms in order to enable analysis and adjustment of both gain and the sense threshold level. In brief, the method consists of three major components. The first is that of detecting the received signals, either R waves or P waves, and making from the sensed waves an amplitude histogram. The amplitude histogram is designed to contain information representative of the distribution of maximum amplitudes of received signals. The digital values, or DSP counts, are first converted into the mV domain and then placed into the histogram, making it possible to use the collected data independent of the momentary gain setting. The next major step is that of detecting data regarding noise, primarily bioelectrical noise picked up by the leads between the implanted device and the heart. Again, an amplitude histogram is made, in the same manner as is done for the sensed R waves or P waves. Following this, an algorithm compares the data of the two histograms and, using predetermined criteria, establishes the wave threshold at a safe level above a floor derived from the noise data.

In order that the event wave and noise amplitude histograms contain accurate amplitude data, it is necessary to use the full range of the A/D converter. In order to provide for this, the invention automatically optimizes the gain as part of the auto sensitivity feature. This is done by the generation of a third histogram, which utilizes unfiltered amplitude data, as described below. Here, unfiltered data is used so as to obtain an accurate picture of the operation of the amplifier. The combination of the adjusted gain and adjusted threshold defines the actual sensitivity setting.

Figure 7:
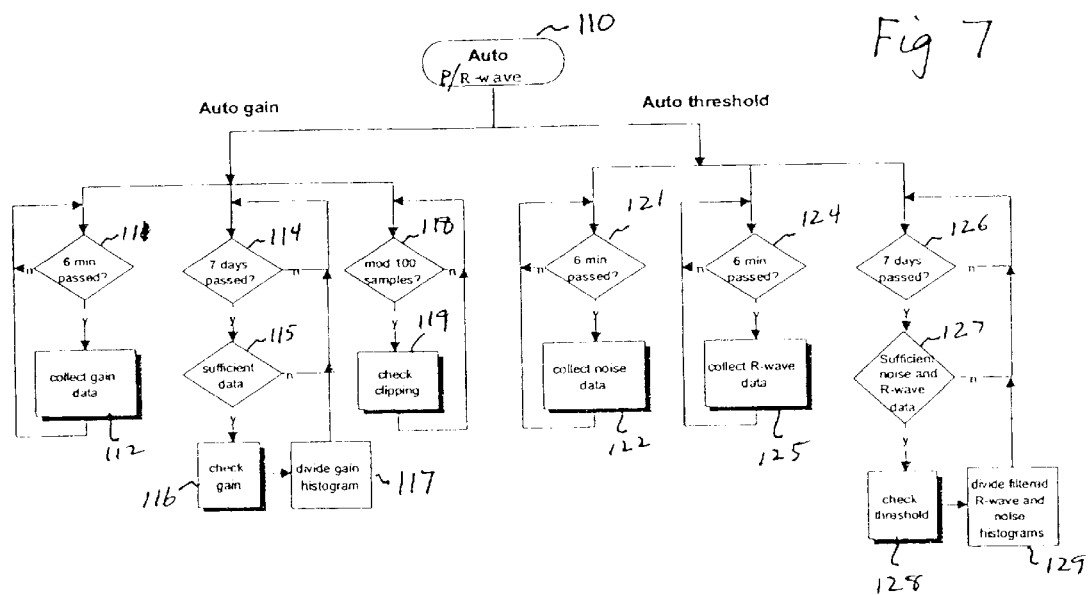
FIG. 7 is a flow chart showing an overview of the steps of this invention that are carried out by software in the preferred embodiment.

FIG. 7 illustrates an overview flow chart of the automatic sensitivity control 110 of this invention. The overview flow chart illustrates the automatic gain control, as well as the automatic sense threshold control which in turn comprises analyzing both noise and signal data. In the illustration of FIG. 7, the signal data is presumed to be R wave data, but the procedure is the same for adjusting threshold for sensing P waves or, indeed, for sensing Twaves.

The determination of auto gain involves utilizing a sample interval of about six minutes, as indicated at step 111. When six minutes has passed, the amplitude of a V-sense is collected in the histogram, as indicated at block 112. This sample rate is subject to adjustment, and may, for example, be within the range of every beat to every hour. However, in the preferred embodiment a low sample rate is utilized in order to reduce the chance of collecting artifacts that occur in bursts, such as with muscle potentials. After a sample has been collected, the clock is reset and the device waits until another 6 minutes has passed.

Amplitude data is collected over a period seven days. Again this is a design choice, and the period may vary from, for example, hourly to monthly. Using the seven-day criteria means that if there has been continuous sensing approximately 1,700 samples are collected during the seven-day period. At block 115, the program checks to see if there is in fact sufficient data. The criterion for this determination suitably is that 100 samples must have been added since the last check. When sufficient data is found, the algorithm proceeds to the check gain block, indicated at 116, and which is discussed in more detail in connection with FIG. 15. The function of this check gain routine is to adjust the gain where necessary. Following this, at block 117, the histogram data is reduced by a predetermined factor, so as to minimize the historical influence of prior collected data. For example, it is proposed to multiply the R wave histogram bins after every threshold check by a factor of one-half (divide by 2). If this is done, the half-life of gathered R wave data will then be one threshold check, or about one week of data under normal circumstances. For P waves, in the preferred embodiment the factor is suitably ⅞, which provides a half-life of five threshold checks, or five weeks. The factor to be used here may, of course, be varied, e.g. between 0.1 and 0.9.

FIG. 7, at blocks 118 and 119, shows an additional gain control feature, for short-term use after device implant. In order to avoid continuous clipping of the received signals during the period just after implant, provision is made to have the physician enable quick gain adjustment. In one embodiment, gain is decreased whenever more than a predetermined number, e.g. 75, out of the last 100 samples have clipped. For this, only two counters need be utilized, namely one for counting events and one for counting the unfiltered signals that have been clipped. At 118, examination of the counter is enabled every 100 events. Clipping is checked at 119 by looking at the counter that holds the clipped signal count, and if excessive clipping is determined gain is decreased accordingly. It is noted that such a fast gain decrease feature could lead to frequent gain switching when the highest R wave (or P wave) amplitudes occur in clusters of more than 100 beats. To prevent such frequent gain switching during the chronic phase, the fast gain control should only be allowed for a short duration, e.g. for one week after implant. This can be provided by automatically limiting this feature to one week or another predetermined period of time following an initialization at implant. Alternately, the system may incorporate a disable mechanism to be programmed by the physician.

The auto sense threshold portions of the overall algorithm are shown on the right side of FIG. 7. There is a noise data collection branch comprising blocks 121 and 122. Noise data is also suitably sampled every six minutes, and when the sample duration has timed out noise data is collected during a predetermined time relative to the signal being analyzed. R wave data is collected during a first window relative to the cardiac cycle; and when P wave data is being collected, the noise data is collected during another window timed according to another set of criteria, as discussed in detail below. After noise is sampled, the noise data is collected in a histogram, as indicated at block 122. Details of the collect noise data routine are set forth in connection with FIG. 14. Also, every six minutes, the collect R wave data routine is run, as indicated at block 125. In this routine, the details of which are set forth in connection with FIG. 15, R wave data is collected and placed in a histogram. Lastly, in connection with the auto sense threshold capability of this invention, every seven days the noise and amplitude data is analyzed to determine whether threshold should be adjusted. When seven days have been timed out, as shown at 126, it is first determined whether there is sufficient noise and R wave data, as indicated at 127. Again, data may be deemed sufficient if at least 100 samples have been added since the last determination. If insufficient data has been received, the routine recycles and waits for sufficient data. When sufficient data has been collected, the algorithm goes to the check threshold routine, indicated at block 128, and discussed in greater detail in connection with FIG. 16. During this routine, in the same manner as was done for gain histogram, the signal and noise histograms are adjusted by dividing (or multiplying) by a predetermined factor which is selected to reduce the historical effect of past data, and to weight the current data which has been obtained during the last seven day period more heavily.

Figure 8A:
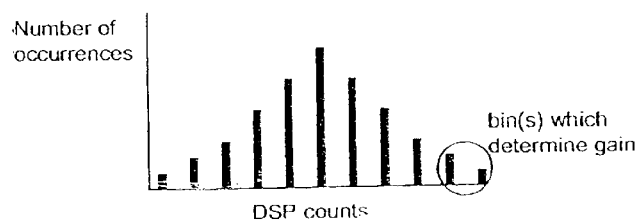
FIG. 8A is an illustration of data in an exemplary gain histogram as employed in this invention.
Figure 8B:
FIG. 8B is a depiction of a preferred arrangement of gain histogram bins in accordance with this invention.

A form of gain histogram is illustrated in FIG. 8A; FIG. 8B shows a preferred arrangement of bin widths. Each of the bars in FIG. 8A represents the number of occurrences where the gain signal had a DSP count within one of the bins. For the gain histogram, the unfiltered signal is used, this being a direct measure of the signal through the gain amplifier. For unipolar sensing, the absolute value of MiU is utilized, since this represents the maximum negative value of the signal. For bipolar sensing, the maximum of either MaU or the absolute value of MiU is used. In the preferred embodiment the DSP range is made symmetrical with respect to positive and negative values. Thus, for a DSP range of −128 to +126 counts, values below −125 or above +125 are placed in a bin representing absolute values of 126 or greater. It is noted that in order to collect data from normal conducted events, which are expected to have the largest amplitude, data is collected only when the pacemaker is in a synchronous state. For R wave sensing, atrial timing is not available for a pacemaker in the VVI mode. Therefore a certain rate criterion needs to be taken into account in order to avoid measuring ventricular tachycardias. For example, the heartbeat interval must be greater than the maximum refractory period plus a safety margin, or greater than 500+100=600 ms. For collecting P wave event data, care must be taken to avoid collecting FFRWs. In order to avoid gain optimization based on FFRWs, events within a window extending from 50 ms before V-pace to 200 ms after V-pace will not be added to the histogram. For AAI mode operation, again a predetermined rate criterion has to be followed, for example, the heartbeat interval must be greater than 650 ms.

In a preferred embodiment, the gain histogram is constructed with exponentially increasing bin widths, using as a base the square root of two. FIG. 8B illustrate 15 bins, with the last (15$^{th}$) bin containing events where the count was greater than 125, thus indicating clipping of the signal. As discussed in connection with the Check Gain routine shown in FIG. 10, the counts in the uppermost bins will be used to determine the degree of clipping and to adjust the gain if there has been too much clipping. The normalized gain setting can also be based upon a square root of 2 base, providing normalized gain from 0.5 to 64 in 15 levels, each higher level having the gain increased by the square root of 2. Of course when the gain is switched one step higher or lower, the gain histogram data should be adjusted to correspond to the new gain. This is easily done by shifting the contents of each bin one step to the left or to the right.

In a preferred embodiment, gain is controlled in such a way that the number of clipped waves is not above an acceptable percentage of the total sensed wave signals. For example, up to 50% clipping may be allowed, under the assumption that for stable R wave or P wave amplitudes, only two or three samples will result in clipped signals, producing relatively little form distortion. The reduction of clipping to at least a minimum degree permits use of the signals a morphology analysis, in an embodiment where that is desirable for additional analysis. While 50% is stated as a preferred percentage of allowed clipping, the device may be programmable to provide a range of percentages, e.g. 10%–90%.

To avoid having the gain jitter between two settings, a hysteresis is implemented by using two different clipping levels, e.g. 40% before the gain is increased and 60% before the gain is decreased. Whenever the gain setting is checked, and the detected clipping rate is not more than 40%, the gain will be increased to the highest setting that will cause at most 40% clipping. However, if the percentage of samples in bin 15, representing all clipped samples with count values equal to or greater than 126, becomes greater than the maximum allowed percentage (60%), then the gain will be decreased one step. Whenever gain is adjusted, the signal is sent through to DSP chip 100 to update the DSP threshold in order to maintain the same sensitivity. Gain is also checked against the S/N requirement as discussed further in connection with the routines of FIGS. 15 and 16. Also, when and as gain is adjusted, the current gain histogram is updated by shifting the bins so that the data in each bin corresponds to the new adjusted gain. When the gain is decreased, the bins are shifted left; data collected in bins that fall outside the updated histogram is discarded. When the gain is increased, the bins are shifted right, and data collected in bins that fall outside the updated histogram is added to the highest bin (15) of the histogram.

Figure 9A:
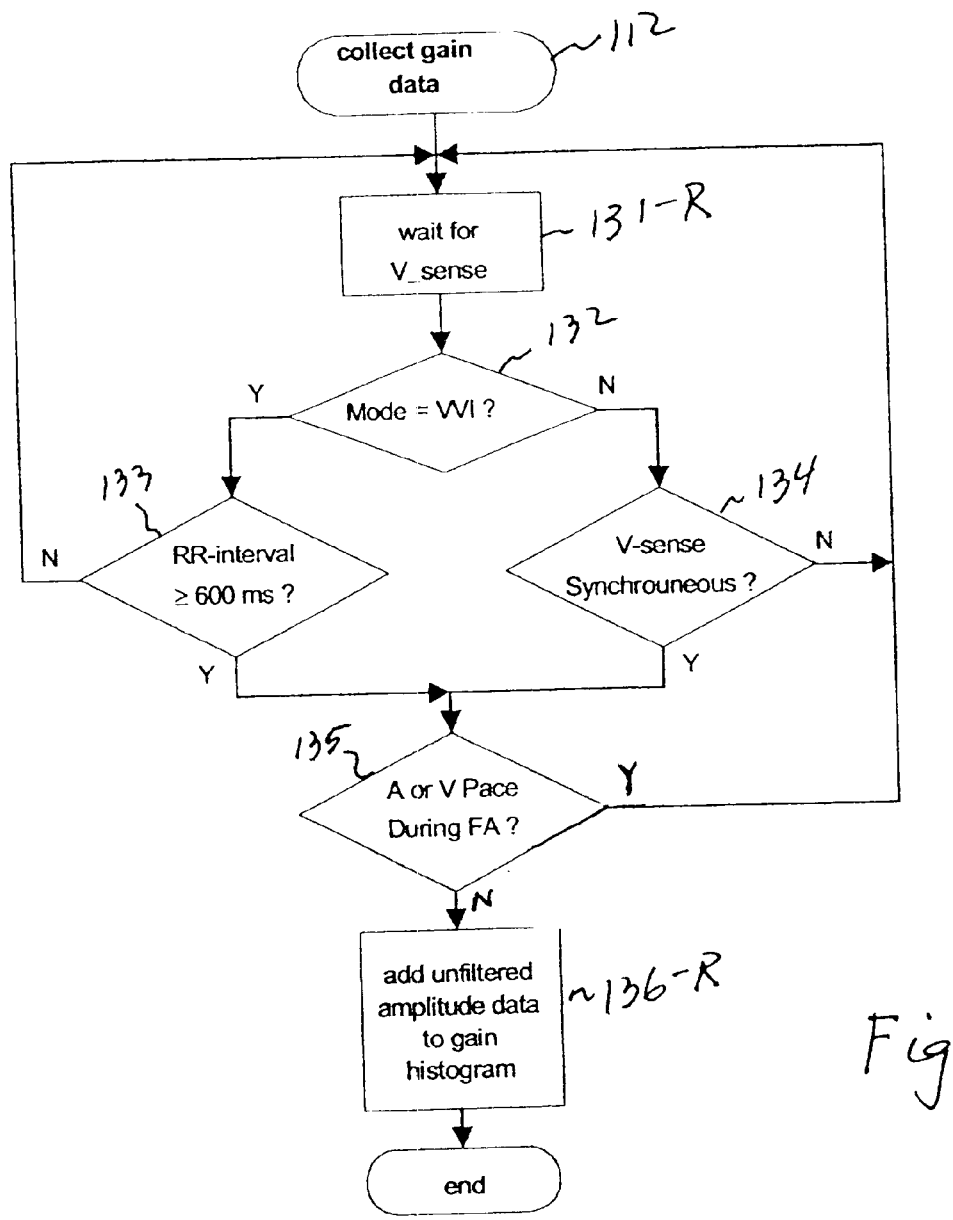
FIG. 9A is a flow chart showing the steps of a preferred routine for collecting gain data, in connection with adjusting gain for an R wave channel.

FIG. 9A is a flow chart showing the primary steps taken in the collect gain data routine 112, as used for adjustment of threshold for the R wave (V_sense) channel. At 131-R, the algorithm waits for receipt of a V_sense signal. When this happens, the device checks to see if it is in a VVI pacing mode, as seen at 132. If yes, the routine branches to 131 and checks to see if the RR interval is at least 600 ms. If no, the data is not valid and the routine goes back and waits for the next V_sense. If the device is not operating in a VVI mode, the algorithm branches to 134 and checks to see if the V_sense is a synchronous event. If no, again it is determined that the data is not valid and the program exits back to wait for the next V_sense. If yes, the routine goes to 135 and determines whether an atrial or ventricular pace was delivered during the Form Analysis activity under taken by the DSP circuitry. When an atrial or ventricular pace occurs during the Form Analysis window, blanking and/or polarization can greatly influence the amplitude measurement, such that it is unlikely to be valid. In such case, the data is rejected and the amplitude measurement must be repeated on the next beat. Likewise, for a PCD type embodiment, the occurrence of a defibrillation or cardioversion output causes the data to be rejected. However, if there has been no A or V pace or other output during the form analysis operation, then the routine goes to block 136-R, and adds the unfiltered amplitude data to the gain histogram. This data represents the absolute value of the minimum unfiltered signal for unipolar sensing, or the greater of either the maximum unfiltered signal or the absolute value of the minimum unfiltered signal for bipolar sensing.

Figure 9B:
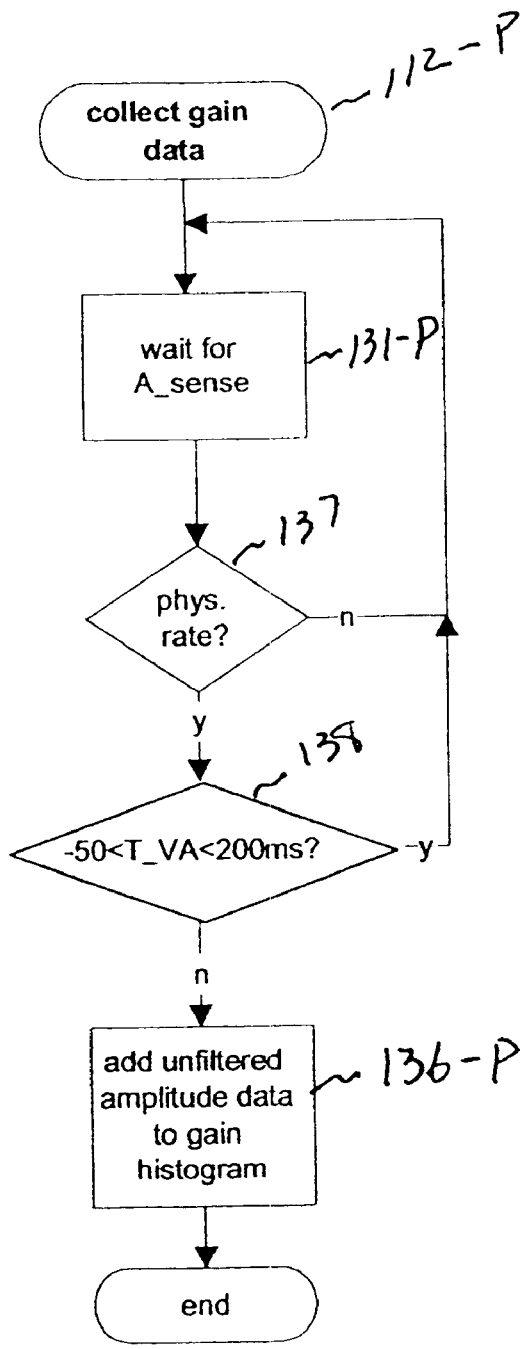
FIG. 9B is a flow chart showing the steps of a preferred routine for collecting gain data, in connection with adjusting gain for a P wave channel, in accord with this invention.

FIG. 9B is a flow chart illustrating the steps for the collect gain data routine 112-P, as used for sensing of P waves. At 131-P, the routine waits for an A_sense. At 137, it is determined whether the sense is within a predetermined physiological rate, or if a pace or other output has been delivered during the analysis. If either criterion is not met, the data is deemed to be unreliable and the routine returns to wait for the next A_sense. If yes, at 138 it is determined whether the event is within a predetermined window of a V-pace, such that it could be an FFRW. If yes, again the data is determined to be unreliable and the routine goes back and waits for the next A_sense. However, if no, at 136-P the unfiltered amplitude data is added to the gain histogram.

Figure 10:
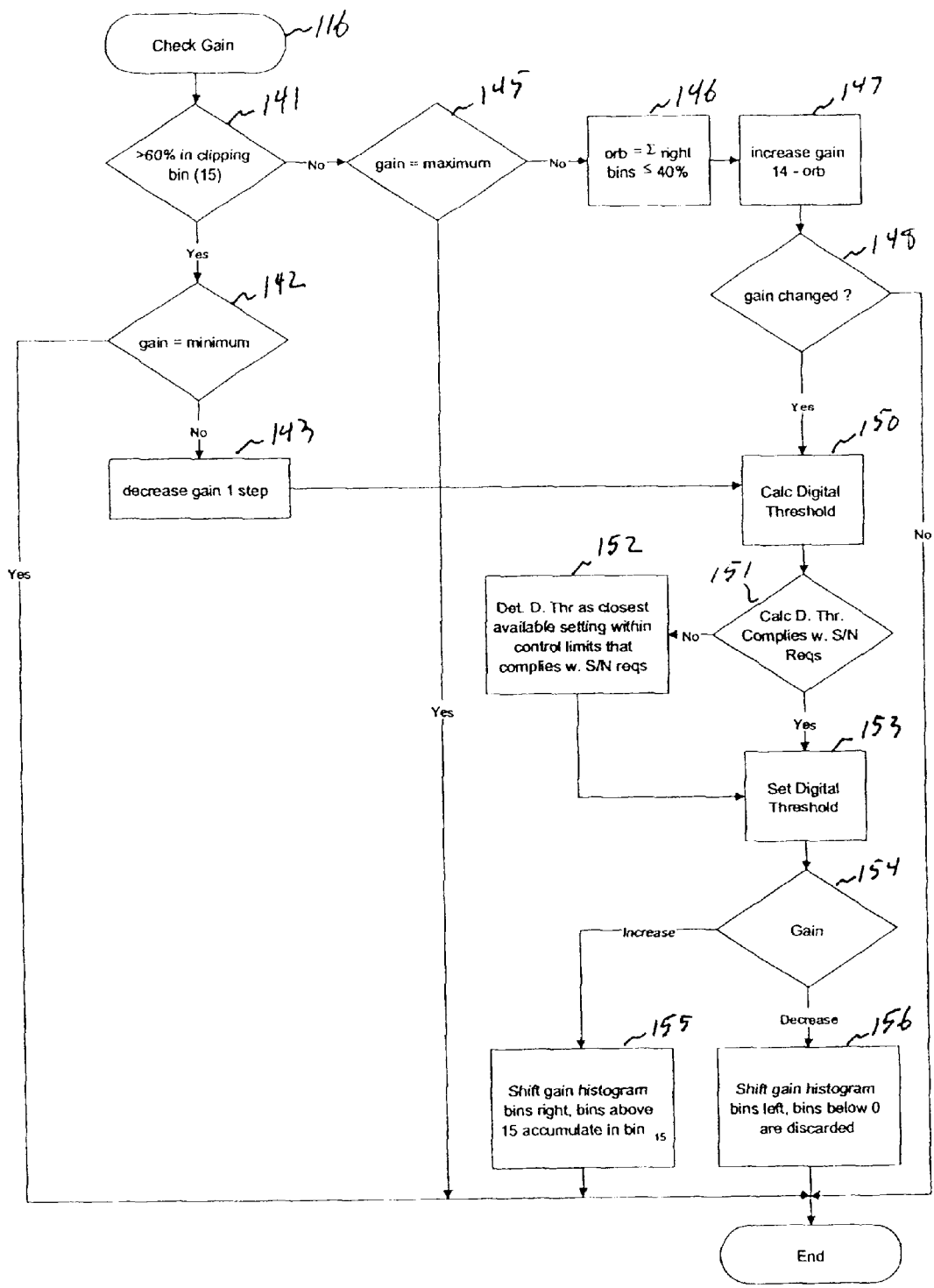
FIG. 10 is a flow chart showing the steps of a preferred embodiment of algorithm for checking gain, in accordance with this invention.

FIG. 10 shows a flow chart for the check gain routine 116, which performs the tasks of determining whether gain needs to be changed, and if so adjusting the gain suitably. At 141, it is determined whether the number of events in bin 15 is greater than 60%. If so, this represents the condition where clipping is unacceptably high and the routine goes to 142 where it determines if gain is already at minimum. If yes, nothing more can be done, and the routine exits. However, if gain is not at the minimum, then at 143 gain is decreased by one step. This results in calculation of the new digital threshold at block 150. At 141, if excessive clipping is not found, the routine checks at 145 to see if gain is already at the maximum value. If yes, the routine exits. If no, the routine goes to 146 and determines the number of right most bins that contain no more than 40% of the DSP events. The value of ORB is established as the Outermost Right Bin that can be kept after gain adjustment without moving gain up to a level where more than 40% of the event signals would be clipped. For example, if bins 15 and 14 contain 38% of the events, and bins 13, 14, and 15 contain 43% of the events, then ORB is 13. In this example, gain can increase by one step, and the amount of expected clipping would still be less than 40%. But if gain were to be increased by two or more steps, then expected clipping would be at least at the 43% level. Accordingly, at 147, ORB is subtracted from 14 to determine the number of steps by which the gain is increased. At 148, it is determined whether this calculation results in a gain change. If no, meaning that ORB was found to be 14, then the routine exits. However, if gain has changed, then the routine goes to 150 and determines a new digital threshold corresponding to the change in gain. At 151, it is determined whether the calculated new digital threshold complies with the S/N requirements, which are discussed in detail below. If no, than at 152 the new digital threshold is determined as the closest available setting within the control limits that complies with S/N requirements. At 153, the digital threshold is set in accordance with the above determinations. At 154, gain is checked to see whether it was an increase or decrease. If it was an increase, then at 155 the histogram is shifted so that the bins go to the right, with the DSP counts in bins above 15 accumulating in new bin 15. If gain has been decreased, then the histogram bins are shifted to the left, and counts in bins shifted below zero are discarded.

Figure 11:
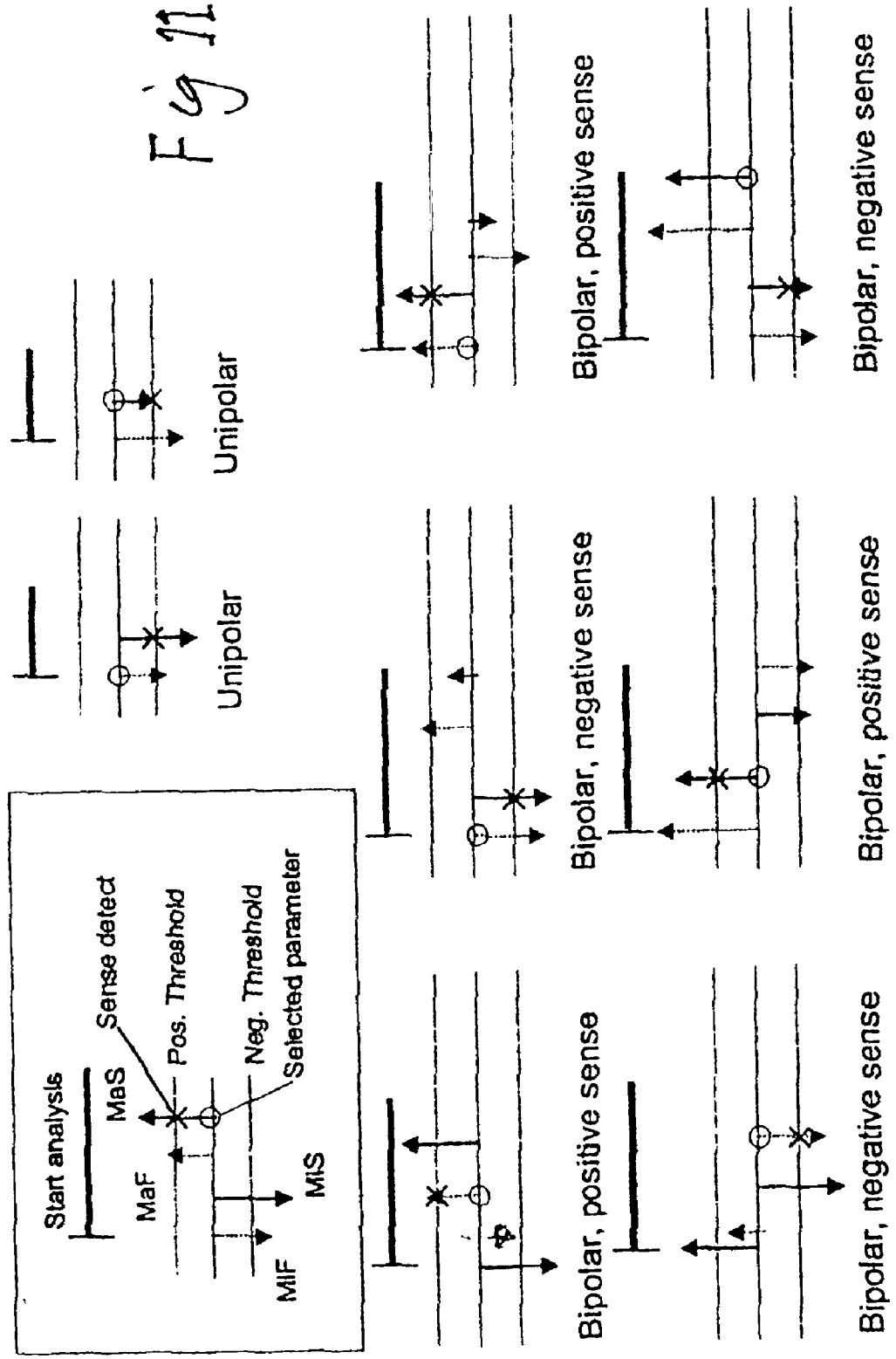
FIG. 11 depicts several examples of determining the occurrence of a signal event, and determining the parameter to be used for histogram data, in accordance with this invention.

The auto threshold branches of the overview flow chart of FIG. 7 can now be examined in detail. Event signal histograms collect all natural activities, either normal conducted R waves or ventricular extra systoles; and P waves. The aim is to optimize threshold based upon these natural activities and not on sensed artifacts such as interference. As indicated above, a DSP signal sense is defined by a combination of threshold crossings of filtered and slope signals in the channel where the operation takes place. A unipolar sense requires the filtered and the slope signal to drop below a certain negative threshold. A bipolar sense requires that both a filtered signal and a slope signal cross a threshold, either positive or negative. FIG. 11 depicts examples of unipolar and bipolar sense sequences, where the legend shows symbols for the different parameters as well as the "Sense detect" and the "Selected parameter". For each example, the sense detection and the selected parameter are shown. The optimal amplitudes are determined by the following mathematical expressions:

| | |
|---|---|
| min(\|MiS\|, \|MiF\|) | for unipolar sensing |
| min(max(\|MaF\|, \|MiF\|), max(\|MaS\|, \|MiS\|)) | for bipolar sensing |

It is to be noted that these expressions are employed in the illustrated embodiment, but other algorithms for determining a sensed event may be employed.

Figure 12A:
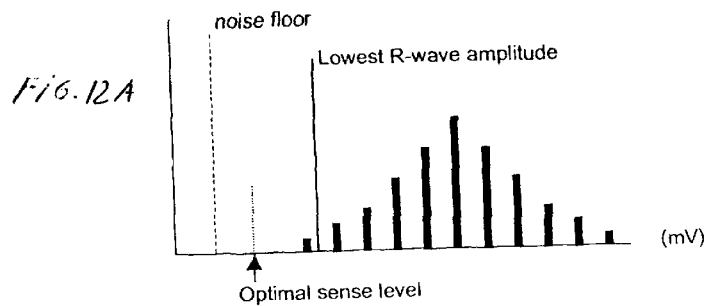
FIG. 12A illustrates an R wave histogram merged with a determined noise floor, and showing the location of the optimal sensitivity level between the lowest R wave amplitude and the noise floor.
Figure 12B:
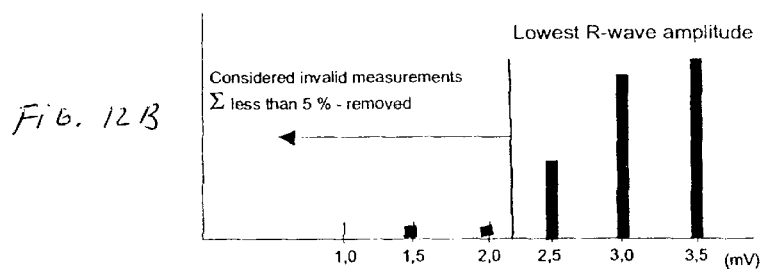
FIG. 12B shows a preferred method of determining the lowest R wave amplitude by discarding bin data containing up to 5% of the R wave amplitude data.

The method of this invention for optimizing sense threshold is illustrated for the case of R wave analysis, but applies similarly to the P wave optimization. A filtered R wave amplitude histogram and a noise floor are utilized to determine the optimal sense threshold, as illustrated in FIG. 12A. The noise floor is based on the collected noise signals derived from electrical noise and continuous bioelectrical noise. In general, the technique is to throw out the lower x % (e.g., 5%) of R wave histogram data, and set the sense level at some point below the lowest remaining Rwave histogram bin and above the determined noise floor. FIG. 12B illustrates the manner of determining the lowest permitted R wave amplitude by removing the bins containing the lowest amplitude data until at least 95% of the total amount of collected samples remains. The lower limit of the lowest bin that still remains filled with data represents the lowest Rwave amplitude. In the example of FIG. 12B, the lowest remaining bin contains DSP counts centered around values corresponding to 2.5 mV, and the lower limit of that bin is shown as being at about 2.2 mV. The collection and analysis of noise data is handled in the same manner as for the R and P wave signals; the same signals and mathematical expressions as set forth above for R and P waves are used for noise.

The noise data is collected by a software start of the DSP analysis window. The analysis window is started after a V event (sense or pace) for R waves; and likewise for a P event. Both start and end of the analysis window are suitably programmable. For P waves, it is proposed to start the collection of noise data 200 ms after completion of the cardiac cycle, to avoid measuring FFRW's as noise. For R waves, the preferred option is to finish the collection of noise data just before the start of noise measurement in the atrial channel, e.g. providing about 6 ms calculation time between the end of the ventricular noise measurement and the start of the atrial noise measurement. For a VVI pacemaker, noise may be measured, for example, for 130 ms following the R sense.

Figure 13A:
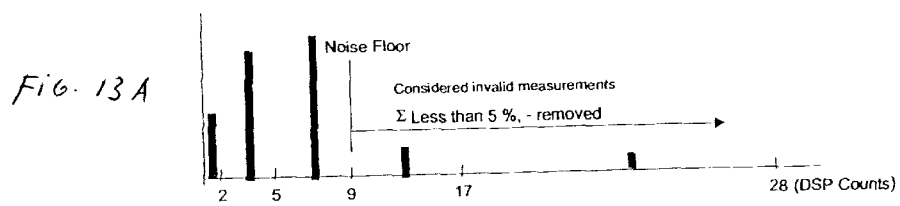
FIG. 13A illustrates a preferred method of determining the noise floor by discarding up to 5% of the noise amplitude data.
Figure 13B:
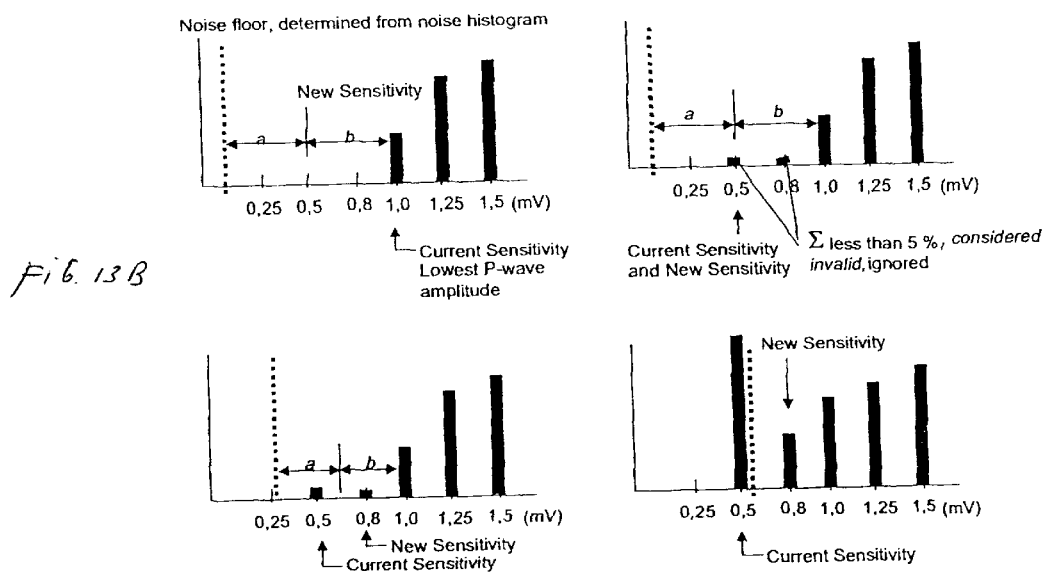
FIG. 13B shows 4 examples of locating the new sensitivity in view of the noise floor and the R wave histogram.

As seen in FIG. 13A, the noise floor estimate is determined by removing noise data bins containing the highest amplitude data until at least 95% of the total amount of collected samples remains. The upper limit of the highest bin that still remains filled represents the noise floor. In the example of FIG. 13A the noise floor is determined to be 9 DSP counts. FIG. 13B illustrates examples of comparing the filtered R wave amplitude histogram and the determined noise floor to check the current sensitivity.

The signal to noise ratio specification that should be met in accordance with this invention provides a minimum digital threshold that can be set for each gain setting. If the algorithm determines a DSP threshold below this minimum, the first available sensitivity with a digital threshold above the minimum value will be selected. To avoid jitter of the sensitivity between two levels, a hysteresis of 10% relative to the previously determined sensitivity is used. This 10% hysteresis is calculated based on the last determined new sensitivity that was in fact utilized to change the sensitivity. The algorithm rules for implementation in the preferred embodiment are as follows:

Determine Real Noise Floor from the noise histogram, in mV.

Project Real Noise Floor into R wave histogram; closest limit of the highest remaining noise bin represents the Noise Floor.

Determine targeted New Sensitivity=Noise Floor+⅓ (lowest sensed R wave —Noise Floor)

Determine difference with targeted New Sensitivity that was determined in the last earlier control cycle.

If difference is less than or equal to 10%, keep the current setting and exit.

If difference is >10%, then:
  Project the targeted New Sensitivity into the R wave histogram and take the low limit of the bin where the targeted New Sensitivity falls as the Proposed New Sensitivity.

If the Proposed New Sensitivity is <1 bin from the Noise Floor, then:
  Set Proposed New Sensitivity=Noise Floor+1 bin. Check to see if the Proposed New Sensitivity falls into the currently set auto-control range; if not:
  Set Proposed New Sensitivity to the closest limit of the auto-control range.

Calculate Proposed New digital Threshold with respect to the current gain setting.

Check whether the Proposed New Digital Threshold complies with S/N requirements. If not:
  Determine the closest less sensitive sensitivity with respect to digital threshold that does and also falls into the auto-control range.

If the Proposed Digital Threshold does not equal the currently set Digital Threshold, then:
  Set the Digital Threshold to the Proposed New Digital Threshold, and
  Save the targeted New Sensitivity for later comparison.

Figure 14:
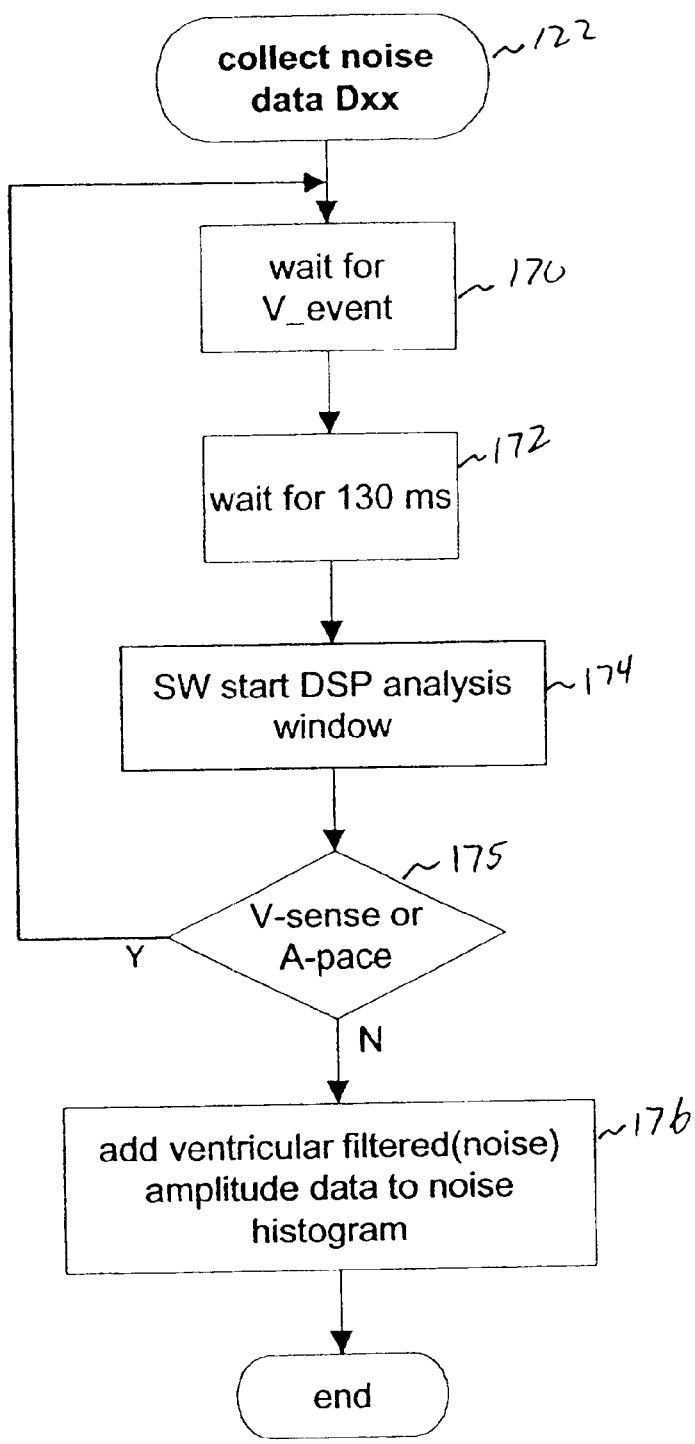
FIG. 14 is a flow chart showing the steps of a routine for collecting noise data, in accord with this invention.

FIG. 14 is a flow chart for routine 122, "collect noise data", illustrated for the ventricular channel. At 170, the routine waits for a ventricular event. At 172, it waits an additional 130 milliseconds, and then sends a signal to start the DSP analysis window, as shown at 174. At 175, a check is made to determine whether a V_sense or an A-pace has occurred during the analysis windows. If yes, as discussed above the data is considered not valid, and the routine goes back and waits for a next ventricular event. However, if there is no V_sense or A-pace during the analysis window, at 176 the filtered noise amplitude data from the DSP chip is added to the noise histogram. In the case of collecting noise data in the atrial channel, at block 172 the device waits for 200 ms. Then, at block 175, instead of looking for a V_sense or an A-pace the routine determines whether the following A_sense has been physiological. If no, the routine branches and goes back to wait for a next Vevent. However, if yes, the atrial filtered noise amplitude data is added to the noise histogram.

Figure 15:
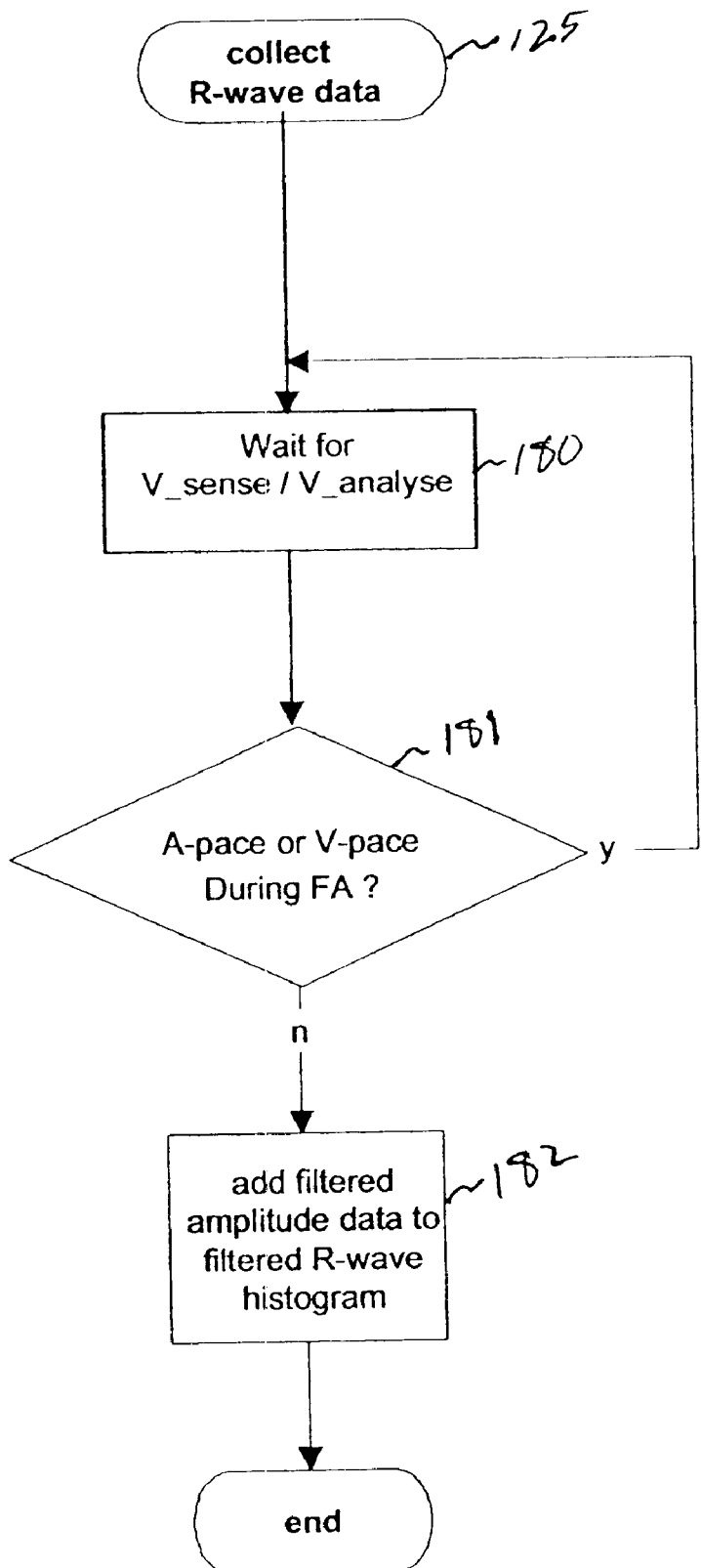
FIG. 15 is a flow chart showing the steps of a routine for collecting signal data, in accord with this invention.

FIG. 15 illustrates a flow chart portion of the algorithm titled collect R wave data (125). At 180, the routine waits for a determination that there has been a V_sense and an analysis of the ventricular signal by the form analysis portion of the DSP. At 181, it is determined whether there has been an atrial or a ventricular pace during the Form Analysis window. If yes, the routine goes back and waits for the next transmission of a V_sense event and the accompanying ventricular signal analysis parameters. If there has been no such pace during the Form Analysis window, then at 182 the filtered amplitude data is added to the R wave histogram. In the atrial channel, for collecting P wave data, at block 180 the algorithm waits for transmission to it of an A_sense event and the parameters provided by the form analysis on the sensed P wave. Following this, at 181 the algorithm determines whether there has been an A-pace or V-pace during FA, and additionally whether the event has taken place within the prohibited time period discussed above (in which case the signal may be an FFRW). If yes, the routine goes back and waits, but if no the filtered amplitude data is added to the filtered Pwave histogram at 182.

Figure 16:
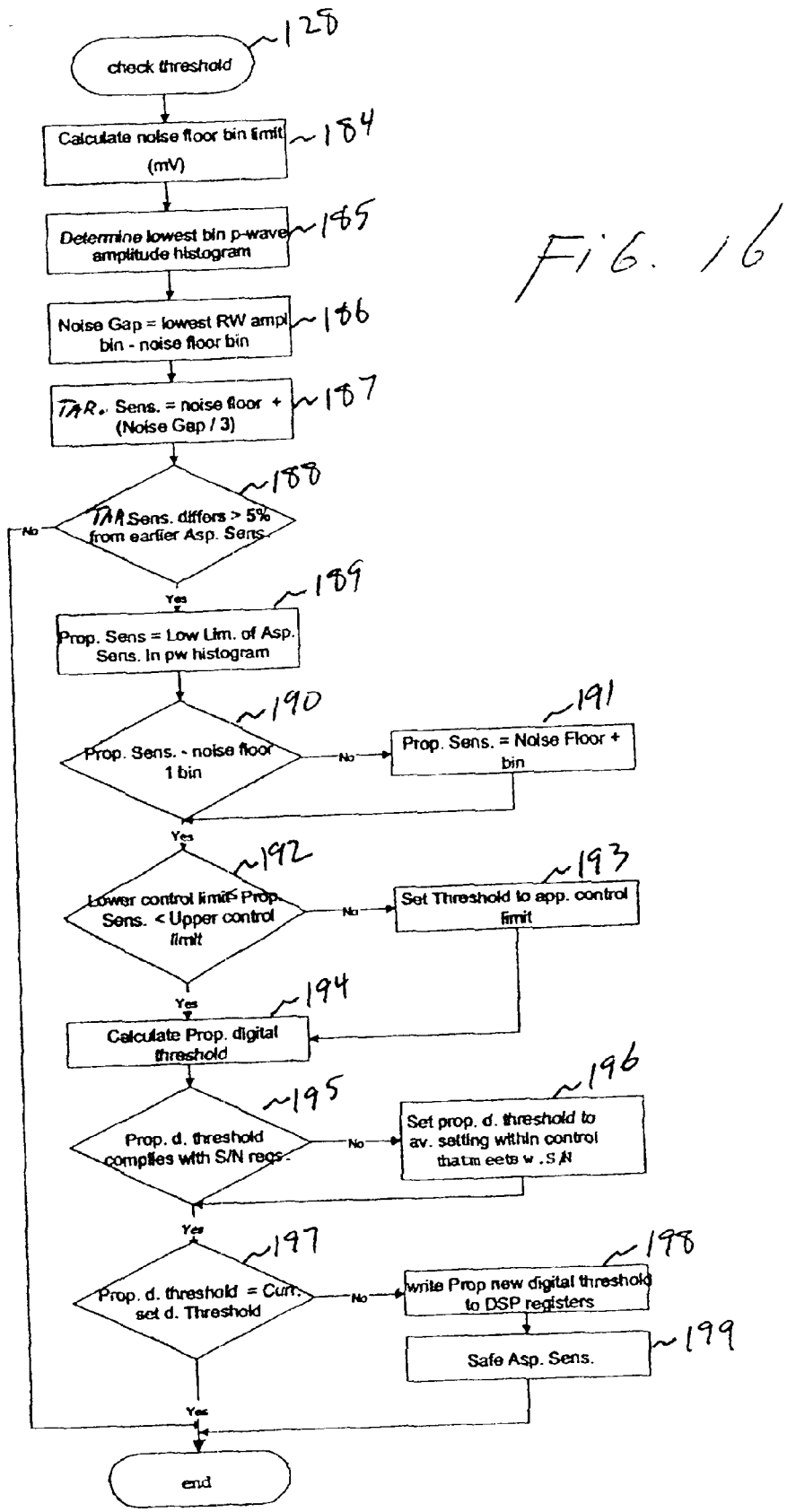
FIG. 16 is a flow chart showing the steps of a routine for checking the threshold level, which sets sensitivity, in accord with a preferred embodiment of this invention.

FIG. 16 shows the algorithm for checking the threshold for either the P or R channel. The steps of the Check Threshold algorithm correspond to the algorithm rules for implementation that are outlined above. At 184, the algorithm calculates the noise floor bin limit, in mV; this is illustrated in FIG. 13A. After this, at 185, the routine determines the lowest bin amplitude histogram. Noise gap is calculated at 186 to be the lowest amplitude bin minus the noise floor bin. At 187, the targeted sensitivity is set equal to the noise floor plus the noise gap divided by 2 for Rwaves or divided by 3 for Pwaves. At 188, it is determined whether the targeted sensitivity differs more than 5% from the earlier computed targeted sensitivity. If no, no change is required, and the routine exits. However, if the answer is yes, at 189 a Proposed Sensitivity is set equal to the lower limit of the histogram where the targeted sensitivity falls. Then, at 190 it is determined whether the Proposed Sensitivity minus the noise floor equals one bin. If no, at 191 Proposed Sensitivity is set equal to the noise floor plus one bin. At 192, the Proposed Sensitivity is compared to the lower control limit and the upper control limit. If it is not between these two limits, then at 193 the threshold is set to the appropriate limit, i.e. the upper control limit if it is not less than the upper control limit, or the lower control limit if it is not greater than the lower control limit.

At 194, the proposed digital threshold is calculated to correspond to the Proposed Sensitivity. At 195, the algorithm checks to see if the proposed digital threshold complies with the S/N requirements, which are programmable. Typically, this requirement is that the lowest possible signal, at the sensitivity threshold, must be at least 20 db above intrinsic system noise. If no, at 196 the digital threshold is adjusted appropriately by determining the closest digital threshold that does meet the S/N requirement. At 197, it is determined whether the proposed digital threshold is the same as the current digital threshold. If no, then the proposed new digital threshold is written into the DSP registers, under control of the microprocessor. The last determined value of targeted sensitivity is saved at block 199. The routine then exits. Note that, as used in claiming this invention, the adjustment of sensitivity means increasing or decreasing the digital threshold, as well as leaving it the same.

The preferred embodiments have been described in terms of organization of data by histograms. As is seen from the above description, this enables accurate manipulation of the data, for determination of the desired gain adjustment and for optimizing sensitivity to mask most noise while receiving most valid signals. The specifics of the algorithms for setting gain and sensitivity achieve the desired objectives, but variations in the steps of these algorithms are within the scope of the invention.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to the use of DSP circuitry. The references to DSP, including the terms DSP channel and DSP circuitry, do not exclude structures or operations that include some conventional analog circuitry. The present invention is also not limited to any particular combination of hardware and software per se, but may find further application with any form of software supplementing hardware. For example, other software embodiments that achieve the ability to efficiently store and manipulate the data, in addition to histograms, are within the scope of the invention. The present invention further includes within its scope methods of making and using the auto-sensitivity control system described hereinabove.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. A cardiac pacing system having a pacing device and a lead for connecting patient cardiac signals to said pacing device, said device having at least one DSP channel having DSP means for amplifying and processing said cardiac signals, said DSP means further having sensitivity means for setting the sensitivity level for use in detection of a said cardiac signal, gain control means for adjusting the gain used in said amplifying, and event means for determining when a said cardiac signal is determined to be a valid cardiac event, further comprising:

amplitude sample means for enabling said DSP means to amplify and process cardiac signals periodically at a first sampling interval in the range of 1 minute to 60 minutes;

amplitude means for obtaining and storing signal amplitude data representative of the amplitude of sampled cardiac signals that have been amplified by said DSP means;

noise sample means for enabling said DSP means to sample noise in said DSP channel following each sampled cardiac signal;

noise means for obtaining and storing noise amplitude data representative of sampled noise in said DSP channel; and check means for comparing said stored signal amplitude data with said stored noise amplitude data periodically at a predetermined check interval greater than at least one hour and for adjusting said sensitivity level in accord with each said comparison.

2. The system as described in claim 1, wherein said gain control means comprises:

clipping means for determining when a sampled signal has been clipped, means for maintaining a running measure of the percentage of sampled signals that have been clipped, and reducing means for reducing gain when said percentage is above a first predetermined clipping percentage.

3. The system as described in claim 2, wherein said gain control means comprises increasing means for increasing gain when said percentage is below a second predetermined clipping percentage.

4. The system as described in claim 3, wherein said gain control means comprises means for setting a clipping level, and gain hysteresis means for setting said first clipping percentage at a predetermined level above said clipping level and for setting said second clipping percentage at a predetermined level below said clipping level.

5. The system as described in claim 2, wherein said gain control means comprises gain histogram means for storing data representative of maximum values of sampled signal amplitudes in a gain histogram having n bins, each said bin containing counts of sampled signals within a respective amplitude range, gain calculation means for calculating gain to be one of n gain levels depending on the contents of said bins, and shift means operative whenever there is a change in gain for shifting the data in said gain histogram to correspond to the change in said gain to a different level.

6. The system as described in claim 5, comprising means for adjusting said DSP sensitivity level to correspond to said calculated gain.

7. The system as described in claim 6, comprising divide means for multiplying the data in each bin of said gain histogram by a predetermined factor in the range of 0.1 to 0.9 after each said check interval to decrease the historical influence of said data.

8. The system as described in claim 5, wherein one of said bins contains a count of signals that were clipped, and said reducing means has means for determining when said count of clipped signals compared to all of the counts in said gain histogram exceeds said first percentage.

9. The system as described in claim 1, wherein said DSP means comprises max signal means for providing digital counts of the maximum amplitude values of said sampled signals, and said amplitude means comprises signal voltage means for converting said digital counts into voltage values and for classifying and storing each said signal voltage value into one of n signal histogram bins.

10. The system as described in claim 9, wherein said DSP means comprises max noise means for providing digital counts of the maximum amplitude values of said sampled noise, and said noise means comprises noise voltage means for converting said noise digital counts into noise voltage values and for classifying and storing each said noise voltage value into one of n noise histogram bins.

11. The system as described in claim 1, comprising check time means for determining when a predetermined check interval in the range of one hour to 1 month has passed, sufficiency means operative at least every check interval for determining if a predetermined sufficient amount of noise amplitude and signal amplitude data has been collected, and activate means for activating said check means whenever such sufficient amount of data has been collected.

12. The system as described in claim 11, wherein said check time means comprises stored interval data representing a check interval in the range of 1 to 14 days, and said sufficiency means comprises stored data representing a count of 10 to 1000 events as a sufficient amount of data.

13. The system as described in claim 11, wherein said amplitude means comprises amplitude histogram means for storing signal amplitude data representative of maximum values of signal amplitudes in a signal amplitude histogram having n bins, each said signal amplitude bin containing counts of sampled signals having representative maximum values within a respective amplitude range, and said noise means comprises noise amplitude means for storing noise data representative of maximum values of noise amplitudes in a noise histogram having n bins, each said noise bin containing counts of sampled noise having representative maximum values within a respective noise amplitude range.

14. The system as described in claim 13, wherein said check means comprises:
 means for discarding data in the lowest bins of said signal amplitude histogram that represent counts up to but no more than a first predetermined percentage of all the counts in said signal amplitude histogram, and then determining the lowest signal amplitude from the lowest remaining bin of said signal amplitude histogram;
 means for discarding data in the highest bins of said noise histogram that represent counts up to but no more than a second predetermined percentage of all the counts in said noise histogram and then determining a noise floor from the highest remaining bin of said noise histogram;
 gap means for determining the gap between said noise floor and said lowest signal amplitude; and
 adjust means for adjusting said sensitivity level to a value represented by said noise floor plus a fraction of said gap.

15. The system as described in claim 14, wherein said DSP channel is an R wave channel, and said adjust means comprises means for setting said fraction to about ½ for R wave detection.

16. The system as described in claim 14, wherein said DSP channel is a P wave channel, and said adjust means comprises means for setting said fraction to about ⅓ for P wave detection.

17. The system as described in claim 14, comprising means for setting each of said first and second predetermined percentages at a level less than about 50%.

18. The system as described in claim 14, comprising means for setting each of said first and second predetermined percentages at about 5%.

19. The system as described in claim 14, comprising multiply means for multiplying the counts in each bin of each of said histograms by a fraction less than one following each adjustment of sensitivity level.

20. The system as described in claim 19, wherein said multiply means comprises means for setting said fraction to a value between ½ and ⅞.

21. An implantable medical device system, said system having signal channel means for receiving and processing medical signals from the patient in whom it is implanted, said channel means having sensitivity means for setting a sensitivity threshold for discriminating between valid signals and noise, said channel means further comprising:
 amplitude sample means for sampling a received signal for a first sample time every predetermined first sample interval and for storing data representative of the amplitude of said sampled signal;
 noise sample means for sampling noise in said channel for a second sample interval that has a predetermined time relation to said first sample time, and for storing data representative of the sampled noise;
 event analysis means for determining a valid signal only when a sampled signal has an amplitude above said sensitivity threshold;
 an amplifier circuit having a signal range with an upper limit and adjustable gain;
 adjust means operable every second interval for processing said stored amplitude data and said stored noise data, said adjust means having gain adjust means for adjusting said gain as a function of the percentage of said sampled signals having a maximum signal amplitude above said upper limit and sensitivity adjust means for adjusting said sensitivity threshold as a function of said stored amplitude data and said stored noise data; and data reduction means for reducing said stored noise data and said stored amplitude data before continuing sampling of data in a manner that gives greater weight to data taken during each second interval than data stored in prior second intervals.

22. The system as described in claim 21, wherein said event analysis means comprises DSP circuitry and means for setting a digital threshold corresponding to said adjusted sensitivity threshold.

23. The system as described in claim 21, wherein said amplitude sample means comprises means for programming said first sample interval to a value within the range of 1 hour to 1 day.

24. The system as described in claim 23, wherein said amplitude sample means comprises signal amplitude histogram means for storing data in n bins, each said bin containing counts of sampled signals having amplitudes within a predetermined range.

25. The system as described in claim 21, wherein said noise sample means comprises noise histogram means for storing data in n bins, each said bin containing counts of sampled noise having amplitudes within a predetermined range.

26. The system as described in claim 21, wherein said noise sample means comprises means for setting said second sample interval to follow said first sample interval by a predetermined delay.

27. The system as described in claim 21, wherein said gain circuit is a DSP circuit and has means for adjusting the gain to one of n gain levels.

28. The system as described in claim 27, wherein said gain adjust means comprises gain histogram means for collecting and storing signal amplitude data in a gain histogram having n bins.

29. The system as described in claim 28, wherein said gain histogram means comprises clipping means for counting in the highest bin the sampled signals that have been clipped.

30. The system as described in claim 29, comprising wherein said gain adjust means comprises means for adjusting said gain when the percentage of clipped signals is greater than a predetermined percentage.

31. The system as described in claim 30, comprising bin shift means for shifting the data in said gain histogram each time that said gain is adjusted.

32. The system as described in claim 21, wherein said adjust means comprises means for programming said second interval to have a value within a range of 1 hour to 1 month.

33. The system as described in claim 32, wherein said data reduction means comprises means for reducing said stored amplitude data and said stored noise data following adjustment of sensitivity threshold each said second interval.

34. The system as described in claim 33, wherein said data reduction means comprises means for reducing said stored amplitude data and said stored noise data by a programmable factor within a range that reduces said data by 0 to 50%.

35. The system as described in claim 21, wherein said event analysis means comprises DSP circuitry, and further comprising software for starting an event analysis during a timed analysis window each said first sample time.

36. The system as described in claim 35, wherein said sensitivity adjust means comprises software for comparing said signal amplitude data and said noise data.

37. The system as described in claim 36, wherein said software comprises means for constructing a signal amplitude histogram and a noise histogram, and comparison means for comparing the signal amplitude bin data with the noise bin data.

38. The system as described in claim 37, wherein said software comprises means for determining a gap between the signal bin data and the noise bin data, and for setting the sensitivity threshold as a function of said gap.

39. The system as described in claim 38, wherein said software comprises means for establishing each of said histograms with exponentially widening bins and said amplifier has exponentially increasing gain levels, whereby recalculation of the bin values is easily done following any gain change.

40. A method of receiving and processing signals from a patient's heart, the method employing an implantable signal channel, comprising:
    setting a first interval of 1 minute to 1 hour, and periodically sampling every said first interval to obtain a heart signal, and storing data relating to each said sampled signal;
    periodically sampling, during a time period in a predetermined time relation to each said sampling of a signal, noise present in said channel, and storing data relating to said noise;
    periodically checking sensitivity in accord with predetermined check criteria, said checking being done after a plurality of said first intervals, said checking comprising:
        removing a first amount of stored signal data according to predetermined signal error criteria to obtain adjusted signal data;
        removing a second amount of stored noise data according to predetermined noise error criteria to obtain adjusted noise data; and
        calculating and setting a sensitivity threshold for detection of valid signals as a function of said adjusted signal and noise data.

41. The method as described in claim 40, comprising:
    calculating a measure of the maximum amplitude of each said sampled signal, and
    determining valid signals as being received only when a said sampled signal has an amplitude measure greater than said sensitivity threshold.

42. The method as described in claim 40, comprising setting said first interval at less than 10 minutes.

43. The method as described in claim 40, comprising periodically checking every second interval, where said second interval is a programmed interval in the range of 1 hour to 1 month.

44. The method as described in claim 43, wherein said checking in accord with predetermined criteria includes the step of determining if there is at least a predetermined amount of sampled signal data and sampled noise data.

45. The method as described in claim 40, comprising amplifying said received signals with a gain adjustable to one of n gain levels, and storing data representative of sampled signal amplitudes in a gain histogram having n bins.

46. The method as described in claim 45, comprising counting clipped signals in the highest bin of said gain histogram, and measuring the percentage of events in said highest bin as the percentage of clipped signals.

47. The method as described in claim 46, comprising adjusting said gain lower when said clipping percentage is greater than a first predetermined percentage.

48. The method as described in claim 47, comprising adjusting said gain higher when said clipping percentage is less than a second predetermined minimum percentage.

49. The method as described in claim 40, comprising storing said sampled signal data in a signal histogram, and storing said noise data in a noise histogram.

50. The method as described in claim 49, comprising removing bin signal data from at least the lowest filled bin of said signal histogram if said bin signal data represents less than a predetermined percentage of the total data in said histogram, and removing bin noise data from at least the highest filled bin of said noise histogram if said bin noise data represents less than a predetermined percentage of the total data in said noise histogram.

51. The method as described in claim 50, comprising determining a gap between the highest remaining noise bin and the lowest remaining signal bin, and setting said sensitivity level within said gap.

52. The method as described in claim 51, comprising multiplying the counts in each of said signal and noise histograms by a factor less than 1 following each setting of sensitivity threshold.

53. The method as described in claim 40, comprising sampling R waves from a patient's heart and setting a sensitivity threshold for detection of valid R wave events.

54. The method as described in claim 53, comprising sampling P waves from a patient's heart and setting a sensitivity threshold for detection of valid P wave events.

55. An implantable cardiac system, having at least one signal processing channel for receiving cardiac signals, said channel having an amplifier circuit with an adjustable gain and having event validation means for validating when a received signal is valid and is not noise, comprising:

gain histogram means for collecting gain data representative of the amplification of sampled ones of received signals and storing said gain data in a gain histogram;

amplitude histogram means for collecting amplitude data representative of the amplitude of said sampled received signals and storing said amplitude data in an amplitude histogram;

noise histogram means for collecting noise data representative of channel noise associated with each sampled signal and storing said noise data in a noise histogram; and setting the gain of said amplifier circuit and setting a sensitivity threshold for said event validation means on a periodic basis and as a function of the data in said histograms.

56. The system as described in claim 55, comprising sampling said received cardiac signals at an interval within the range of 1 minute to 1 hour, carrying out said setting of gain and sensitivity threshold after at least a predetermined amount of data has been obtained and stored in each of said histograms, and reducing the data in each of said histograms by a respective predetermined measure after each said setting of gain and sensitivity threshold.

* * * * *